United States Patent [19]

Mazess

[11] Patent Number: 5,673,298
[45] Date of Patent: *Sep. 30, 1997

[54] DEVICE AND METHOD FOR ANALYSIS OF BONE MORPHOLOGY

[75] Inventor: Richard B. Mazess, Madison, Wis.

[73] Assignee: Lunar Corporation, Madison, Wis.

[*] Notice: The term of this patent shall not extend beyond the expiration date of Pat. No. 5,291,537.

[21] Appl. No.: 689,863

[22] Filed: Aug. 15, 1996

Related U.S. Application Data

[63] Continuation of Ser. No. 477,053, Jun. 7, 1995, Pat. No. 5,577,089, which is a continuation-in-part of Ser. No. 344,328, Nov. 23, 1994, abandoned, and Ser. No. 241,270, May 10, 1994, Pat. No. 5,509,042, which is a continuation-in-part of Ser. No. 67,651, May 26, 1993, Pat. No. 5,291,537, which is a division of Ser. No. 944,626, Sep. 14, 1992, Pat. No. 5,228,068, and a continuation-in-part of Ser. No. 73,264, Jun. 7, 1993, Pat. No. 5,306,306, which is a continuation of Ser. No. 862,096, Apr. 2, 1992, abandoned, which is a continuation of Ser. No. 655,011, Feb. 13, 1991, abandoned.

[51] Int. Cl.$^6$ .............................. G01B 15/04; G01N 23/06
[52] U.S. Cl. ................................. 378/54; 378/55; 378/58
[58] Field of Search ........................... 378/54, 56, 57, 378/53, 55, 58, 62, 98; 128/665, 653.1

[56] References Cited

U.S. PATENT DOCUMENTS

| | | | |
|---|---|---|---|
| 3,423,657 | 1/1969 | Ponstingl et al. | 318/33 |
| 3,576,997 | 5/1971 | Slavin | 250/90 |
| 3,639,764 | 2/1972 | Olson et al. | 250/83 |
| 3,659,099 | 4/1972 | Bertheau | 250/50 |
| 3,866,047 | 2/1975 | Hounsfield | 250/360 |
| 3,946,234 | 3/1976 | Hounsfield | 250/363 |
| 4,228,357 | 10/1980 | Annis | 250/445 |
| 4,475,122 | 10/1984 | Green | 358/101 |
| 4,593,406 | 6/1986 | Stone | 382/44 |
| 4,721,112 | 1/1988 | Hirano et al. | 128/659 |
| 4,788,429 | 11/1988 | Wilson | 250/363 |
| 4,811,373 | 3/1989 | Stein | 378/54 |
| 4,903,203 | 2/1990 | Yamashita et al. | 364/413 |
| 4,915,112 | 4/1990 | Singer | 128/653 |
| 4,922,915 | 5/1990 | Arnold et al. | 128/653 |
| 4,961,425 | 10/1990 | Kennedy et al. | 128/653 |
| 4,971,069 | 11/1990 | Gracoetsky | 128/781 |
| 5,005,195 | 4/1991 | Lanza et al. | 378/62 |
| 5,033,073 | 7/1991 | Friddell | 378/146 |
| 5,034,969 | 7/1991 | Ozaki | 378/18 |
| 5,049,748 | 9/1991 | Ito et al. | 250/327 |
| 5,068,788 | 11/1991 | Goodenough et al. | 364/513 |
| 5,123,056 | 6/1992 | Wilson | 382/6 |
| 5,132,996 | 7/1992 | Moore et al. | 378/65 |
| 5,138,553 | 8/1992 | Lanza et al. | 364/513 |
| 5,172,695 | 12/1992 | Cann et al. | 128/653 |
| 5,210,688 | 5/1993 | Cheu et al. | 364/413 |
| 5,222,201 | 6/1993 | Lis | 395/120 |
| 5,224,035 | 6/1993 | Yamashita et al. | 364/513 |
| 5,228,068 | 7/1993 | Mazess | 378/54 |
| 5,247,934 | 9/1993 | Wehrli | 128/653 |
| 5,270,651 | 12/1993 | Wehrli | 324/308 |
| 5,348,009 | 9/1994 | Ohtomo et al. | 378/54 X |
| 5,365,564 | 11/1994 | Yashida et al. | 378/55 |

FOREIGN PATENT DOCUMENTS

| | | |
|---|---|---|
| 411155 | 6/1991 | European Pat. Off. . |
| 2098425 | 5/1981 | United Kingdom . |

OTHER PUBLICATIONS

Measurement of leg Length Inequalities by Micro–Dose Digital Radiographs, Joseph F. Altongy, M.D. et al., Journal of Pediatric Orthopaedics, 7:311–316, 1987.

(List continued on next page.)

*Primary Examiner*—David P. Porta
*Attorney, Agent, or Firm*—Quarles & Brady

[57] ABSTRACT

A method for automatically analyzing the morphometry of bones from data obtained by lateral digital scans of the bone obtains a matrix of data values assembled from an x-ray scan. The matrix is analyzed to locate an axis of the bone from which subsequent measures may be referenced. Once the axis is fixed, one or more of several useful indicia of bone condition such a length or interbone spacing can be calculated. The measures are compared to a set of reference values that has been normalized to lumbar vertebrae of the patient.

6 Claims, 13 Drawing Sheets

OTHER PUBLICATIONS

The Automatic Assessment of Knee Radiographs in Osteoarthritis Using Digital Image Analysis, J.E. Dacre et al., British Journal of Rheumatology 1989; 28:506–510.

X–Ray Measurement Predicts Fracture Odds, Imaging News, Jun. 1993, pp. 9,10, H. Carswell.

Geometric Measurements From Dual X–Ray Absorptiometry Scans Predict Hip Fracture, K.G. Faulkner et al., University of California, San Francisco, Abstract 98. No date.

Predicting Femoral Neck Strength From Bone Mineral Data, A Structural Approach, Thomas J. Beck, ScD. et al., Invest. Radiology 25:6–18, Jul. 18, 1989.

Development of a new radiographic scoring system using digital image analysis, J.D. Dacre, et al., Annals of Rheumatic Diseases, 1989; 48, 194–200.

Expert Image Quality, Lunar Corporation. No date.

J.D. Adams et al., "Methodological Studies, Bone Mineral Density Reference Ranges Across Populations", pp. 14–16 in E.F.J. Ring (ed) Current Research in Osteoporosis & Bone Mineral Measurement 11:1972.

Change in Vertebral Shape in Spinal Osteoporosis, L. R. Hedlund et al., 1989, Calcif. Tssue Int. 44:168–172.

A Comparison of Morphometric Definitions of Vertebral Fracture, Journal of Bone and Mineral Research, 6:25–34, 1991, R. Smith–Bindman et al.

Guidelines for Clinical Trails in Osteoporosis, J.A. Kanis et al., 1991, Osteoporosis Int. 1:182–188.

Measurement of Vertebral Area on Spine X–rays in Osteoporosis: Reliability of Digitizing Techniques, P. Nelson et al, Journal of Bone and Mineral Research, 5:707–716, 1990.

A newly developed spine deformity index (SDI to quantitate vertebral crush fractures in patients with osteoporsis, H.W. Minne et al., Bone and Mineral, 3:335–349, 1988.

Normal Vertebral Dimensions and Normal Variation in Serial Measurements of Vertebrae, Journal of Bone & Mineral Resarch, K.M. Davies et al., 4:341–349, 1989.

P.D. Ross et al., Pre–Existing Fractures & Bone Mass Predict Vertebral Fracture Incidence in Women, Annals of Internal Medicine, 114:919, 1991.

G. Leidig et al., A study of complaints and their relation to vertebral destruction in patients with osteoporosis, Bone and Mineral, 8:217–229, 1990.

L.R.Hedlund et al., Vertebral morphometry in diagnosis of spinal fractures, Bone and Mineral, 5:59–67, 1988.

J.C. Gallagher et al., Vertebral morphometry: normative data, Bone and Mineral, 4:189–196, 1988.

M.D. Murphy et al., Nondisplaced Fractures: Spatial Resolution Requirements for Detection with Digital Skeletal Imaging, Radiology, pp. 865–890, 1989.

P.D. Ross et al., Ability of Vertebral Dimensions from a Single Radiograph to Identify Fractures, Calcif. Tissue Int., 51:95–99, 1992.

L. Mosekilde et al., Normal Vertebral Body Size and Compressive Strength: Relations to Age and to Vertebral and Iliac Trabecular Bone Compressive Strength, Bone 7, 207–212, 1986.

J.E. Harrison et al., Bone Mineral Mass Associated With Postmenopausal Vertebral Deformities, Bone and Mineral, 10:243–251, 1990.

P.Bernecker et al., The spine deformity index in osteoporosis is not related to bone mineral and ultrasound measurements, 1992, British Journal of Radiology, 65:393–349.

Minne et al., "A newly developed spine deformity index (SDI) to quantitate vertebral crush fractures in patients with osteoporosis", *Bone and Mineral*, (1988) pp. 335–349.

M.K.Keerekoper et al., Vertebral Fracture or Vertebral Deformity?, Calcif. Tissue Int. 50:5–6, 1992.

T. E. Keats, Measurement of Vertebral Body Height & intervertebral Disc Width: Dorsal and Lumbar Regions, Atlas of Roentgenographic Measurement, 6th Edition, 1968.

P. Sauer et al., Spine Deformity Index (SDI) Versus Other Objective Procedures of Vertebral Fracture Identification in Patients with Osteoporosis: A Comparative Study, Journal of Bone and Mineral Research, 6:227–238, 1991.

Vertebral Deformity Indices, Influence of X–ray Technique & Patient Width, J. W. Kuper et al., Erasmus University Rotterdam. No date.

Steve Cummings, Guidelines for Assessing Vertebra Fractures, Vertebral Fracture Workshop, Sep. 1992.

Kalendar et al., Bone Mineral Measurement: Automated Determination of Midvertebral CT Section, Radiology 1988.

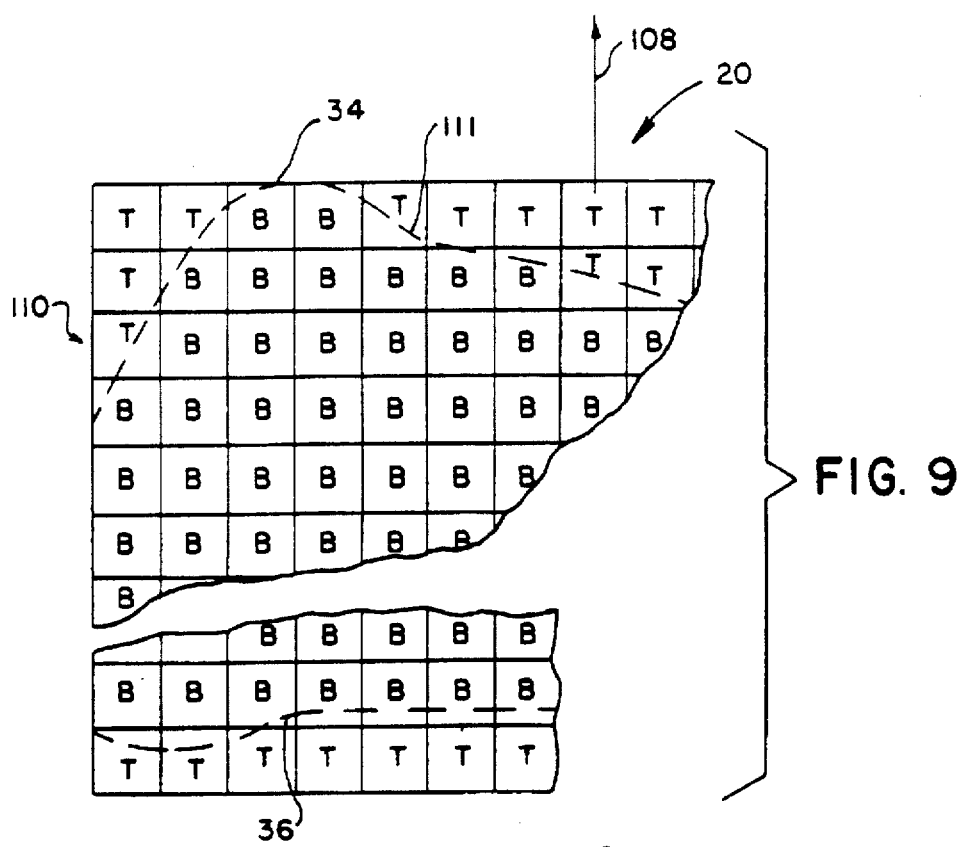
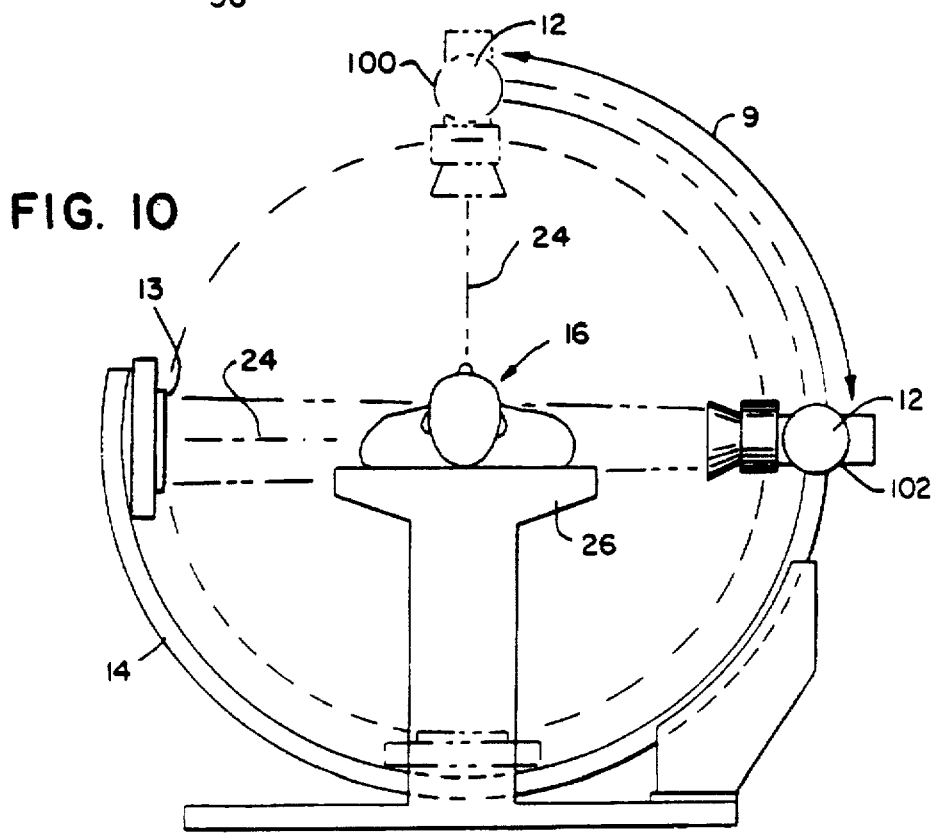

DEVICE AND METHOD FOR ANALYSIS OF BONE MORPHOLOGY

FIELD OF THE INVENTION

This is a continuation of application Ser. No. 08/477,053 filed Jun. 7, 1995 now U.S. Pat. No. 5,577,089 which is a continuation-in-part of application Ser. No. 08/344,328 filed Nov. 23, 1994 abandoned, and a continuation-in-part of application Ser. No. 08/241,270 filed May 10, 1994 now U.S. Pat. No. 5,509,042, which is a continuation-in-part of application Ser. No. 08/067,651 filed May 26, 1993, now U.S. Pat. No. 5,291,537 which is a divisional of application Ser. No. 07/944,626 filed Sep. 14, 1992, now U.S. Pat. No. 5,228,068; and a continuation-in-part of application Ser. No. 08/073,264 filed Jun. 7, 1993, now U.S. Pat. No. 5,306,306, which is a continuation of application Ser. No. 07/862,096 filed Apr. 2, 1992, abandoned, which is a continuation of application Ser. No. 07/655,011 filed Feb. 13, 1991, abandoned.

The present invention relates to the general field of bone densitometry and vertebral morphology and relates, in particular, to an automated technique and apparatus for the determination and analysis of vertebral morphology utilizing techniques of bone densitometry.

BACKGROUND OF THE INVENTION

Digital bone densitometry devices such as the DPX machines manufactured by LUNAR Corporation of Madison, Wisconsin or the QDR machines manufactured by Hologic, Inc. of Waltham, Massachusetts, are used to generate broadly based values of bone character, such as bone mineral content ("BMC") or bone mineral density ("BMD"). Such information about bone character, and in particular, about bone character in the spine is often relied on to diagnose and treat bone depletive disorders such as osteoporosis. In the case of osteoporosis, bone density measurements alone are not definitive for diagnosis. The clinician must also look for evidence of spinal fracture. J. A. Kanis, et al. Osteoporosis Int. 1:182–188 (1991) Determining whether a fracture is present is important both on clinical grounds and for research purposes. In the clinical setting, a patient may display a reduced BMD but the clinician is hesitant or unwilling to begin a particular treatment regimen without a diagnosis of fracture or deformity. In the research setting, diagnosis of fracture is important in studying the incidence and prevalence of osteoporosis in a population, or as an entry criterion to a clinical study, or as a measure of efficacy with regard to a particular treatment. In this regard, the European Foundation for Osteoporosis has published guidelines for clinical trials in osteoporosis which recommends a definition of osteoporosis as a "disorder where one or more fractures has arisen due to an increase in the fragility of bone," and an endpoint of fracture reduction in studies of efficacy of new drugs for the treatment of osteoporosis. J. A. Kanis, et al.

While the presence or absence of vertebral fracture is critical in the diagnosis of osteoporosis, diagnosis of vertebral fracture is often difficult. Over one-half of such fractures are asymptomatic, and in cases of minimal symptoms obvious fracture or deformity will often not be observed particularly if there is no previous radiological record for comparison.

Vertebral morphometry techniques promise to make the determination of vertebral fracture or deformation more objective. These approaches rely on certain indexes or normative values of vertebral body dimensions. See e.g. Minne et al., "A Newly Developed Spine Deformity Index (SDI) to Quantitate Vertebral Crush Factors in Patients with Osteoporosis," *Bone and Mineral*, 3:335–349 (1988); J. C. Gallagher et al., "Vertebral Morphometry: Normative Data," *Bone and Mineral*, 4:189–196 (1988); Hedlund et al., "Vertebral Morphometry in Diagnosis of Spinal Fractures," *Bone and Mineral*, 5:59–67 (1988); and Hedlund et al., "Change in Vertebral Shape in Spinal Osteoporosis," *Calcified Tissue International*,44:168–172 (1989).

In using vertebral morphometry to diagnose fractures, the clinician commonly employs analog radiological imaging techniques. In essence, an analog x-ray image of the patient's vertebrae is taken, and printed onto a fixed media, such as an x-ray radiographic film print. The print is made to a specific scale relative to the original human, i.e., one-to-one, or a specifically reduced or expanded scale. Then the clinician manually measures the size of a vertebra by using a ruler and a straight edge and actually draws on the film to outline the vertebral body, and then measures with the ruler between criteria lines drawn onto the film itself.

There have been recent efforts to computerize this morphometric technique. See e.g. Nelson, et al., "Measurement of Vertebral Area on Spine X-rays in Osteoporosis: Reliability of Digitizing Techniques", *J. Bone and Mineral Res.*, Vol. 5, No. 7:707–716 (1990); Smith- Bindman et al., "The index of radiographic area (IRA): a new approach to estimating the severity of vertebral deformity ", *Bone and Mineral*, 15:137–150 (1991). These efforts still rely on first obtaining an analog X-ray image of the vertebra, digitizing the analog image and then manually selecting the points of measurement.

Thus the clinician diagnosing or treating osteoporosis must, at a minimum, use two relatively expensive medical devices: a bone densitometer and an X-ray imaging device. Further, morphometric techniques which rely on analog radiography are complicated by image magnification. The analog radiographic image is typically 10–15% larger than life-size, and the magnification is variable depending on the location of the object relative to the plane of the radiograph. In particular, the front edge of the object, away from the radiographic plate is more magnified than the back edge toward the radiographic plate. The result is that bone edges perpendicular to the plane of the plate, which for morphological measurement should produce a sharp visual demarcation on the fan beam radiograph, produce a blurred boundary. Distortions of the spine are particularly acute for cone beam exposures at the edges of the cone beam where the beam is most angled. For vertebral morphology the angulation obscures and distorts intervertebral spacing at the top and bottom of a field rendering morphological measurements, for example of body height, imprecise. This impreciseness is exacerbated by the imposition of human error when it is left to the clinician to manually select the measurement point. Variation will often necessarily exist between clinicians and between measurements by the same clinician at different times. These problems apply, not just to the detection of osteoporosis, but to morphometric measurements of bone in general.

While bone densitometers such as the DPX and the QDR devices are capable of generating images, the image quality of these present day bone densitometers is inferior to the common analog X-ray imaging machine. This is particularly true for scanning systems where resolution is intentionally limited to prevent the need for an overly long scanning time. Thus, the imaging capability of bone densitometers has not been relied on for diagnostic purposes and until the present invention, bone densitometry systems have not been used to determine bone morphology, or to analyze the relationships of bone structures.

The use of vertebral morphometric data to diagnose vertebral fractures such as may indicate osteoporosis is complicated by the need to develop standard measurements for healthy individuals in the population. In the case of vertebral height measurements, the detection of fracture requires that the measured height values be compared to standard height values for similar healthy individuals. These standard values will vary according to the height, weight, sex, and other characteristics of the individual being measured. Accordingly, multiple standards values must be developed and ancillary measurements must be made of the individual to properly identify the appropriate standard to be used for the individual. The development of the multiple standard values and the matching of the correct standard value to a patient is time consuming and subject to error.

SUMMARY OF THE INVENTION

The present invention recognizes that although the variation in vertebral morphometric measurements may be great among individuals, the vertebral morphometric measurements for a given spine follow a relatively predictable pattern. Accordingly, it is possible to employ a single set of reference values (that may be scaled appropriately) to provide a reference for vertebral morphometric measurements for many different individuals. The scaling of this set of reference values is accomplished by evaluating two or more reference vertebrae and extracting a measured index that reflects the general morphometry of the measured individual. This measured index is then used to scale the set of reference values and the scaled set of reference values is used as a reference to evaluate the particular vertebral measurements for the individual.

Specifically, the invention provides a method of evaluating a human spine comprising the steps of measuring the height of at least two lumbar vertebra of a patient and mathematically combining these heights to produce the measured index for the patient. Heights of other vertebra of the patient are then measured and compared to corresponding heights of the set of reference values normalized by the measured index for the patient. Deviations from values for a healthy individual may then be easily detected.

It is thus one object of the invention to permit measured vertebral morphometric parameters to be compared with a single set of references values for a healthy individual minimizing the need to further characterize the measured individual as to height, weight, sex or other ancillary characteristics. The measured index used to tailor the standard value to the particular individual is extracted from the measured individual him or herself through the measurement of one or more lumbar vertebra.

It is another object of the invention to provide a robust measured index value. The lumbar vertebrae provide a number of advantages in this regard. They have a relatively low incidence of fracture so they may serve as a reference value even for osteoporotic individuals. They are larger so the effects of measurement errors are reduced. They are clearly visualized in a lateral spine image, being clear from ribs. They do not exhibit the large motion artifacts often seen in scanning images of the thoracic spine. Use of multiple lumbar vertebrae further improves the reliability of the measured index.

The set of reference values as normalized by the measured index may be used to estimate the positions of the superior and inferior border of superior vertebra in the spinal column of the measured individual-and in particular to estimate those positions in vertebra whose images may be obscured by ribs and other tissue. These estimated positions may be used to define regions of analysis for the purpose of automated vertebral morphometry.

Thus, it is another object of the invention to permit semi-automated vertebral morphometric analysis on vertebrae that may be poorly imaged by constraining the analysis region to prevent the semi-automatic procedure from misidentifying the locations of the vertebral endplates.

In a similar fashion, the semi-automated procedure may be constrained by user inputted reference lines.

Thus, it is another object of the invention to permit computer augmented vertebral morphometry on poorly imaged vertebrae.

Other objects, advantages, and features of the present invention will become apparent from the following specification when taken in conjunction with the accompanying drawings.

BRIEF DESCRIPTION OF THE DRAWINGS

FIG. 9 is a schematic diagram of the bone mineral density values over a portion of a vertebra illustrating one method of determining the borders of a vertebra wherein for clarity the density values within a range associated with tissue are shown by the letter "T" and the density values in a range indicating bone are shown by the letter "B";

FIG. 10 is a view of the instrument of FIG. 1 along the scanning direction showing movement of the source and detector between a lateral position and an anterior- posterior position as performed in one embodiment of the present invention;

DESCRIPTION OF THE PREFERRED EMBODIMENT

Hardware

Figure 1:
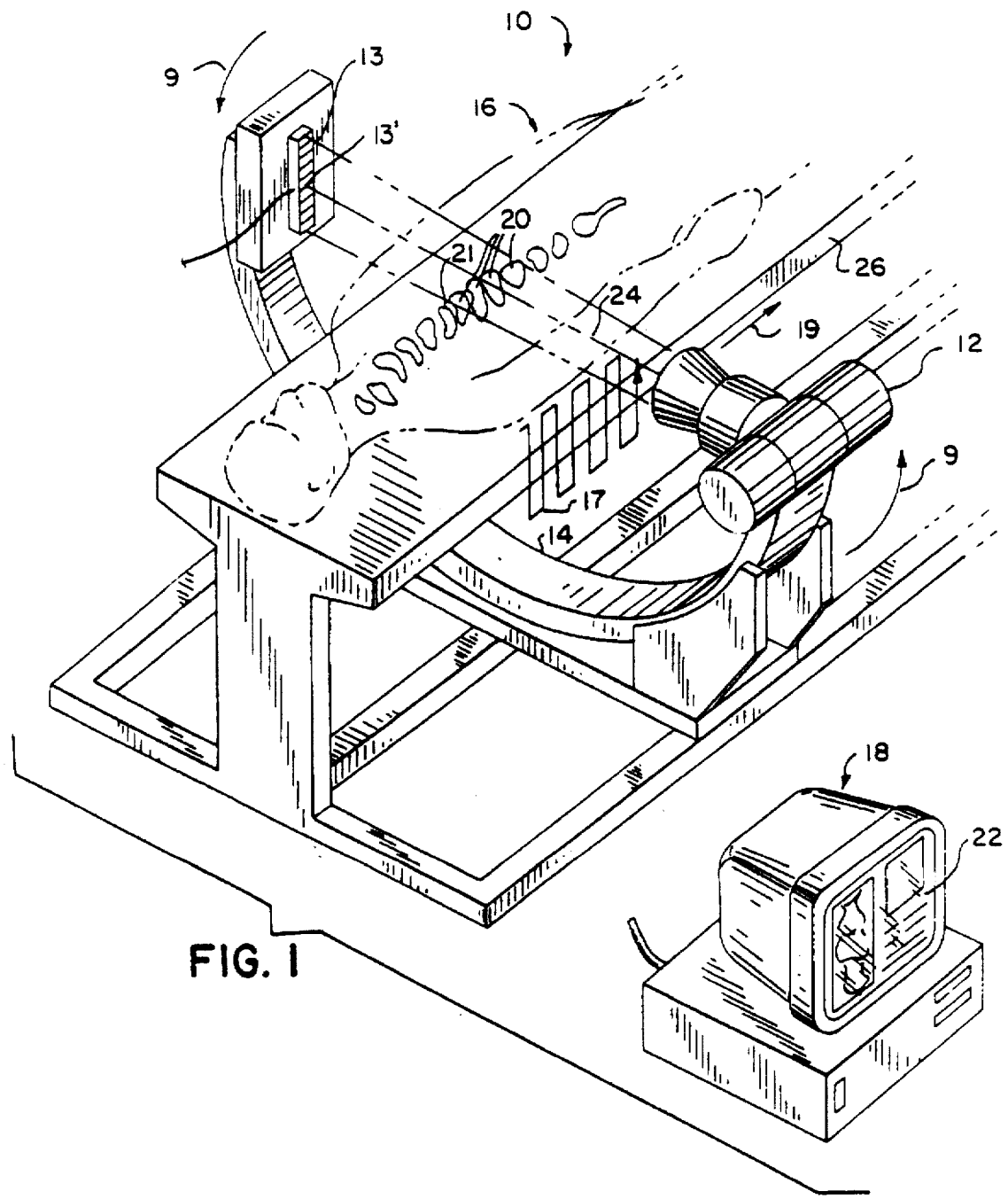
FIG. 1 is a schematic illustration of an instrument for use in the present invention showing a first embodiment employing a pencil beam and a raster scan and a second embodiment employing a fan beam and a linear scan.

Shown in FIG. 1 is a simplified schematic of an X-ray based digital x-ray device 10 of the type described in the preferred embodiment of the present invention. The digital x-ray device 10 includes a dual energy X-ray radiation source 12 and a detector 13, both of which are mounted on a rotatable C-arm 14, which extends on either side of a supine patient 16 so as to direct and receive radiation along a radiation axis 24 through the patient 16. The C-arm 14 is designed to be rotated in a vertical plane as indicated by arrows 9 so as to allow both an anterior-posterior ("AP") view of the spine or other bones or a lateral view of the same. The C-arm 14 may also be moved longitudinally along the patient's body as indicated by scanning direction arrow 19 and may be positioned under the control of servo motors as is understood in the art.

The digital x-ray device 10 of the preferred embodiment, has the capability of switching from a dual energy X-ray to a single energy X-ray or polychromatic X-ray mode. By single-energy X-ray is meant ionizing radiation at a narrow band of energies of a few keV in the diagnostic imaging range (20–100 keV) or a polychromatic beam such as is conventionally emitted from an X-ray source. Switching from dual energy to single energy may be done either by affecting the source, e.g., removing or adding a K-edge filter, or by switching energies, i.e., switching between high and low x-ray tube voltage, or by affecting the detector e.g. selecting only one energy level during a particular study, or a combination of source and detector.

The digital x-ray device 10 of the preferred embodiment also has the capability of selecting between a fan beam of x-rays which is collimated and oriented toward the vertebra such that the plane of the fan beam and detector is perpendicular to the longitudinal axis of the spine or a pencil beam being substantially the centermost ray only of the fan beam along the radiation axis 24. When the fan beam configuration is selected, the detector 13 is a linear array of detector elements subtending the fan beam for providing simultaneous measurements along a number of rays of the fan beam associated with each such detector element. When the pencil beam configuration is adopted, only a limited number of detector elements 13' are employed and measurement is made only along the single ray of the pencil beam. A cone beam (not shown in FIG. 1) may also be used, in which case the detector 13 is matrix of rows and columns of detector elements covering the area of the fan beam opposite the patient 16.

The fan beam, when used, is scanned along the longitudinal axis of the spine or scanning axis 19. The use of a narrow fan beam perpendicular to the spine allows imaging of the spine, or other long bones generally aligned with the spine such as the femur, with minimal distortion along the longitudinal axis resulting in the ability to measure vertebral dimensions in this axis with greater accuracy than possible with a cone beam. For greater accuracy in the horizontal axis, the fan beam may also be oriented so that the vertebral body or other bone is irradiated by the center portion of the beam rather than the edges which are subject to distortion. Since the center of a fan beam has little angulation the resulting data is comparable to that obtained with a pencil beam and yet a scan can be obtained much faster.

Alternatively, when the pencil beam is used a raster scan 17 of the lateral view of the vertebral body is done. The raster scan moves the radiation axis back and forth in the anterior-posterior direction along successive scan lines separated in the longitudinal direction so that the radiation axis moves generally along the scan direction 19. The raster scan 17 results in the slower acquisition of data but provides the least distortion.

If a cone beam is used, the digital output must be reformatted to compensate for ray alignment in order to allow more accurate measurement of dimension. The cone beam acquisition may be performed at discrete stationary locations or may be acquired continuously as the radiation axis 24 is scanned along the scan direction 19. The rotatable C-arm 14 carrying the radiation source 12 and the detector 13 is connected to, and operates under the control of, a general-purpose digital computer 18, which is specifically programmed for use in operating the digital x-ray device 10 and analyzing the data and includes specialized algorithms for carrying out the calculations required by the present invention. In addition, the present invention includes a data acquisition system ("DAS") and a data storage device (both of which are not shown) and may be included in the computer 18 and a display means 22 for outputting the data analysis. As is understood in the art, the computer also includes a keyboard and cursor control device (not shown) for user input.

Figure 11:
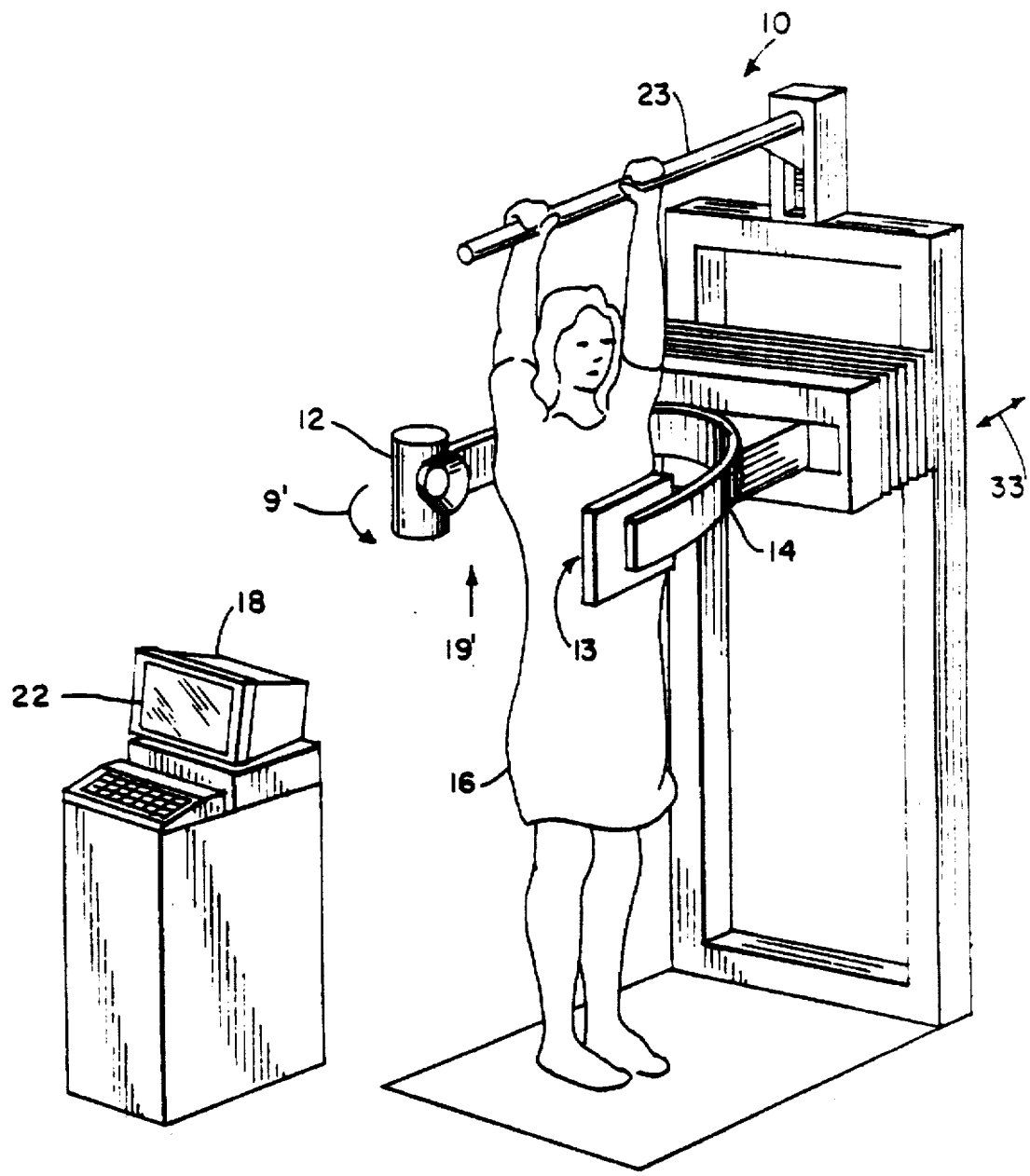
FIG. 11 is a schematic illustration of an instrument for use in the present invention showing a third embodiment in which the patient is scanned in a standing position.

Referring now to FIG. 11, in a second embodiment of the digital x-ray device 10', preferable for use in studies where the patient's spine and other bones should be under the natural load imposed by the weight of the patient's body, the patient 16 remains in a standing position with the hands above the head resting on a horizontal grip bar 23 positioned above the patient's head. In this embodiment the source 12 and detector 13 rotate about a vertical axis and the C-arm 14 on which they are mounted rotates in a horizontal plane as indicated by arrow 9'.

The C-arm 14 may be moved vertically along the patient's body as indicated by direction arrow 19' and may be translated in a horizontal plane as indicated by arrow 33 to provide complete flexibility in allowing overlapping scans of the patient 16 for studies that involve a wider path than is subtended by the detector array 13. In other respects, the vertically oriented digital x-ray device 10' operates analogously to its horizontal counterpart shown in FIG. 1.

A single digital x-ray device 10 may be advantageously employed for both standing and supine studies of the patient 16 by incorporating a pivot (not shown) in the supporting structure of the digital x-ray device 10 so that it may swing from the vertical position of FIG. 11 to the horizontal position of FIG. 1 for the different types of studies. It will be understood to those of ordinary skill in the art that the other components of the devices of FIG. 1 and FIG. 11 are common to both and thus that this design may provide a flexible, cost effective machine.

In most general terms, the radiation source 12 emits radiation of a certain energy level or levels along the radiation axis 24 at defined locations along the scan. The radiation passes through the vertebral body 21 being scanned and is then received by the detector 13. The analog output of the detector 13 is sampled and digitized so as to produce a signal consisting of discrete data elements by a data acquisition system ("DAS") which may then transmit the digitized signal to the computer 18 which stores the data in computer memory (not shown) or on a mass storage device.

Vertebral Analyses Software

Figure 5:
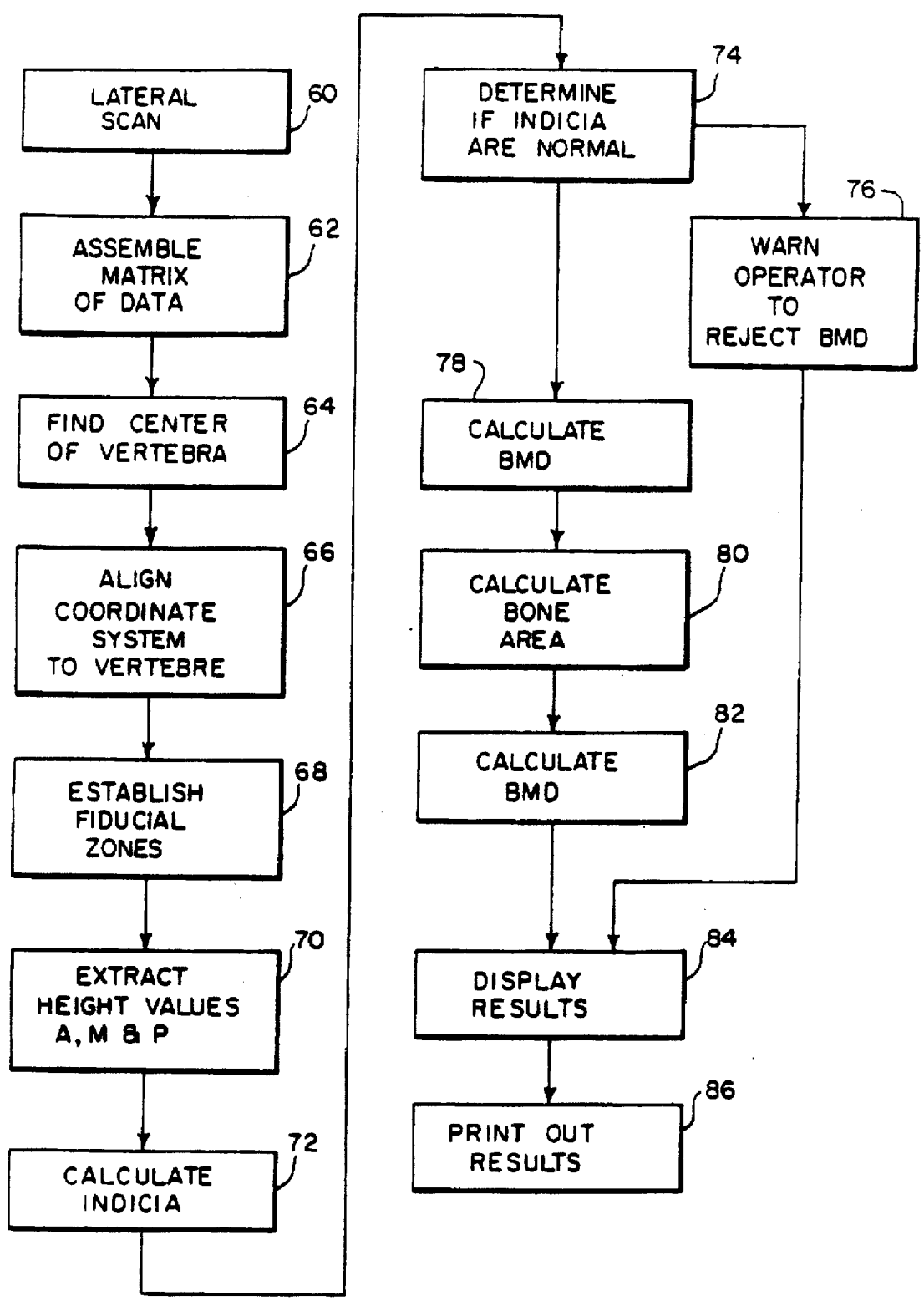
FIG. 5 is a flow chart illustrating the method of the present invention in analyzing vertebral morphology.

As can be seen by reference to FIG. 5, once scanning of the patient 16 by the source 12 and detector 13 are completed, as indicated by process block 60, the computer 18 of the present invention arranges the data elements obtained in the scan in a matrix per process block 62. Each data element of the matrix is associated with a spatial location defined by the position of the C-arm 14 when the data element is acquired during the scan. The spatial locations among the data elements differ by the distance the instrument, e.g., the source 12 and detector 13, moves between taking each data point, both laterally and (in the case of the pencil beam) vertically between scans.

For a digital x-ray device 10 such as that in FIG. 1 which uses a fan beam, data elements are taken in a series of scans by moving the X-ray source 12 and detector 13 in short longitudinal steps. If a pencil beam is used, data elements are taken in short vertical scans in the anterior-posterior direction. In either case the matrix of data elements is assembled from a series of these scans to collect data over an area defined by the length of the scan along the longitudinal scanning 19 or the vertical lines of the raster scan 17.

In studying the morphology of the human vertebra, it is preferred that the scan be taken from a lateral direction through the subject's spine and a single energy mode is selected. Each data element has a relative value proportional to the amount of radiation absorbed by the tissue at the corresponding location. In turn, the absorption of radiation by a tissue correlates to certain physical properties of that tissue. For example, bone absorbs a lesser amount of radiation than does soft tissue. The data elements thus obtained, are referred to PBM for pseudo bone mineral content. The numbers are pseudo values because they are non-calibrated and therefore dimensionless. At this point in the analysis, therefore only the relative differences between the data elements are significant, not their absolute values. While the calibration for each data element could be done at this point, it is consumptive of computer resources, and thus is deferred at this point and the PBM values are used. The matrix of values thus obtained is a representation of the relative density of the patient's vertebra viewed laterally.

Once the matrix is assembled, the computer 18 automatically conducts a local comparison of data elements to determine the juncture of data elements attributable to bone and data elements attributable to soft tissue. In order that the purpose and the results obtained from such a scan may be readily understood, reference is had to FIG. 2 which illustrates an idealized set of vertebrae 20. Each of the vertebrae 20 has characteristic boundary regions indicated by the reference numbers in FIG. 2 with respect to a single vertebra. Each of the vertebrae has an anterior border 30, a posterior border 32, a superior border 34, and an inferior border 36. Additional elements of the vertebrae 20 located rearward of the posterior border are referred to as the posterior elements 38. The region between adjacent vertebrae 20 is referred to as the intervertebral zone and is indicated at 40.

Superimposed on L4, the lowest of the illustrated vertebrae 21 of FIG. 1, is a series of horizontal lines, representing the raster scans 17 of the digital x-ray device 10 as employed when the digital x-ray device 10 is operating with a pencil beam. The results of that raster scan is the matrix of digital values, with each point value in a single scan being displaced one unit distance from the previous measured digital value.

Figure 2:
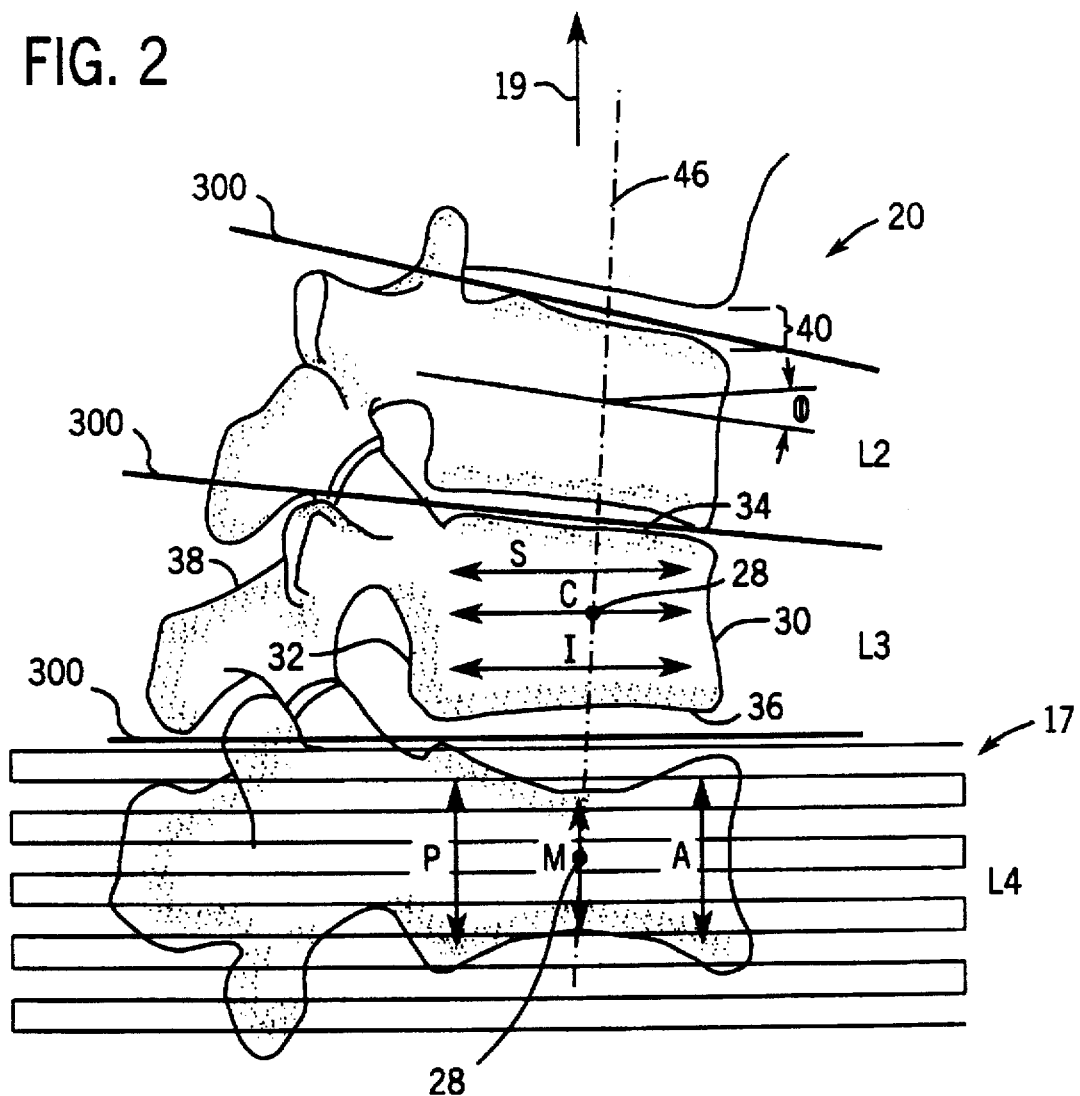
FIG. 2 is an illustration of a lateral view of vertebrae illustrating measurements used in determining the indicia used in the present invention.

Referring to FIGS. 1 and 2, the patient 16 is supported in the supine position on a table 26 so that the vertebrae 20 of the spine are generally aligned with the scan direction 19. Nevertheless, it will be recognized that because of the curvature of the spine, the angle of the vertebrae 20, i.e., the angle of the anterior border 30, a posterior border 32, a superior border 34, and an inferior border 36 with respect to the scan direction 19 will vary among vertebrae 20. Whereas this variation may be accommodated by the trained eye of a physician in estimating the distances that describe the morphology of the vertebrae 20, for the automation of such measures, the orientation of the vertebral body 21 with respect to the raster 17 or the scan direction 19 must be established to provide repeatable and accurate morphology measurements.

The first step in evaluating the relative placement of a vertebral body 21, indicated by process block 64 of FIG. 5, is a determination of the approximate location of each vertebrae 20 as identified by its approximate center 28. The centers 28 are located by evaluating the horizontal and vertical histograms of FIGS. 3 and 4.

Figure 4:
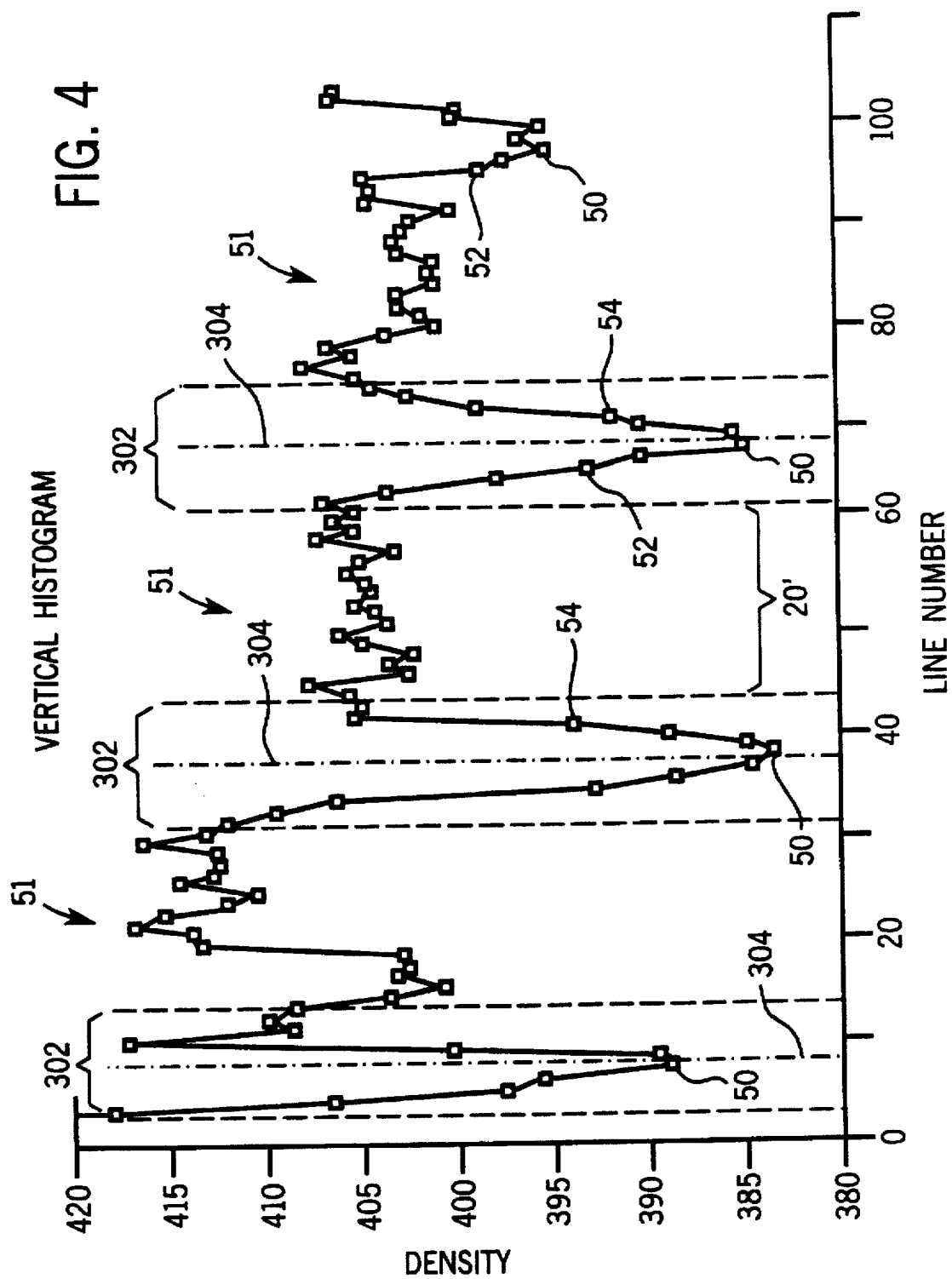
FIG. 4 is a histogram illustrating a set of data points in a vertical cross-section of a vertebra.

Shown in FIG. 4 is a superior-inferior histogram of the spinal column of vertebrae 20. The vertical axis of the histogram represents the units of body density measured at the detector 13 while the horizontal axis represents the spatial locations of data elements along a line such as indicated at 46 in FIG. 2. Ideally, line 46 is centered along the spine as positioned by several arbitrary horizontal histograms of adjacent vertebrae 20 as will be described below. Alternatively, the histogram of FIG. 4 may represent not the data elements along a single line 46 but an average of data elements along anterior-posterior lines.

Generally, when a pencil beam is used, the data elements in the vertical histogram are not derived from a single line of raster scan 17 of digital x-ray device 10 but rather are reassembled using suitable digital techniques from the entire matrix of data elements collected by the digital x-ray device 10. As reassembled, the values of the histogram of FIG. 4 represent a sequential series of data elements taken in a superior-inferior direction. This set of data elements is equivalent to the result which would be obtained from a single superior-inferior scan.

Note that the histogram of FIG. 4 includes local minima 50 and local maxima 51. These minima 50 represent areas of low density and the maxima 51 represent areas of high density. The location of the intervertebral zones 40 are readily ascertainable as the local minima 50 and the approximate inferior border 52 and superior border 54 of the vertebrae 20 are recognizable as the portions of the histogram on either side of the local minima 50. The superior-inferior centers of the vertebrae may be identified as points halfway between the local minima 50.

At this point, the lateral spine image is displayed to the user with the intervertebral spaces demarcated as horizontal lines 300. A cursor control device, such as a track ball or mouse, may be employed by the user to adjust these lines if necessary with the identified minima 50 of the vertical histogram being adjusted accordingly.

The user then identifies on the image any one of the lumbar vertebra L1 through L5 with the cursor control device. The remaining vertebra are automatically numbered in sequence according to the sequence of demarcation lines 300 and these numbers are displayed adjacent to the image of the corresponding vertebrae.

Figure 3:
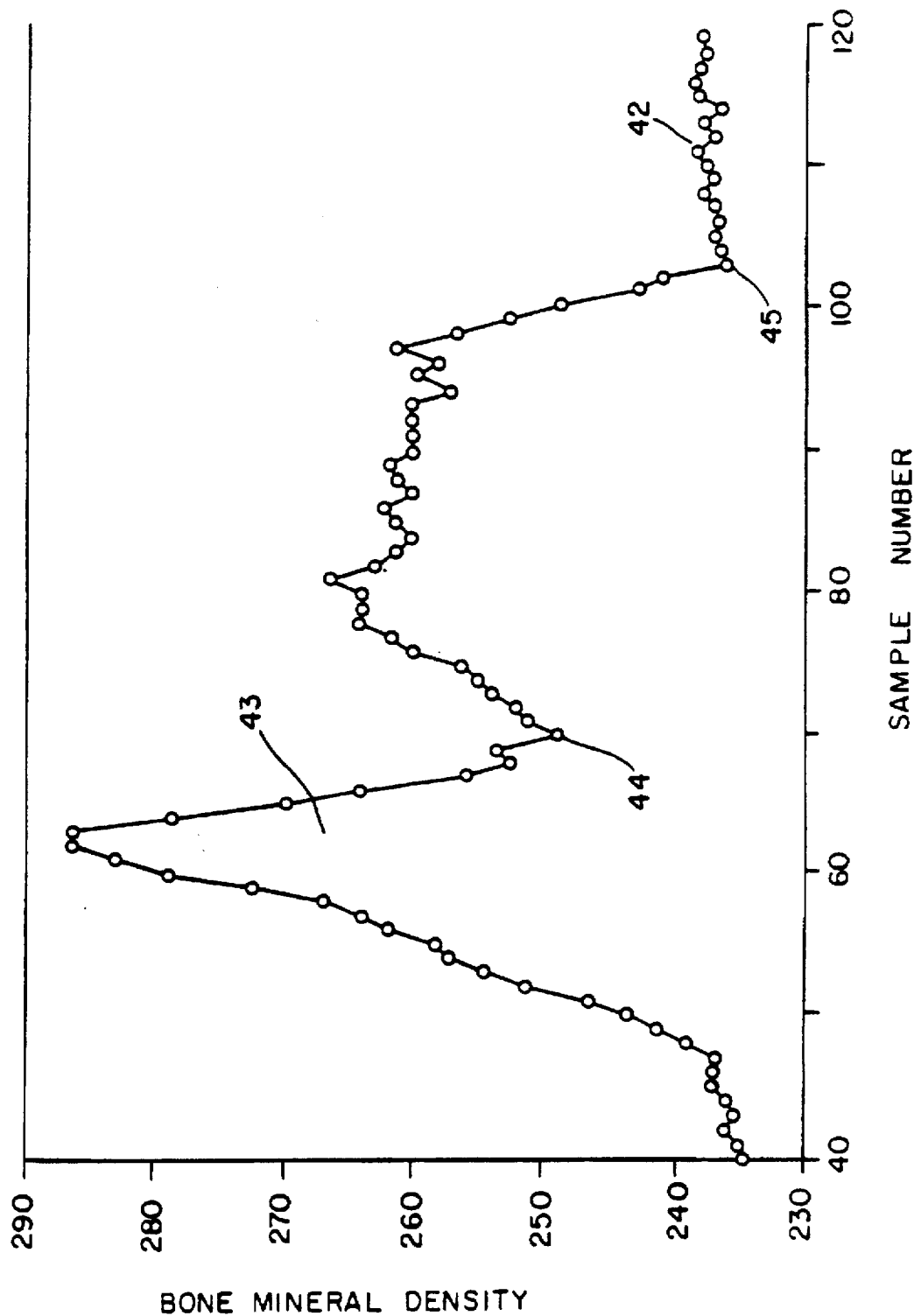
FIG. 3 is a histogram illustrating a set of data points in a horizontal scan of a vertebra such as that illustrated in FIG. 2.
Figure 6:
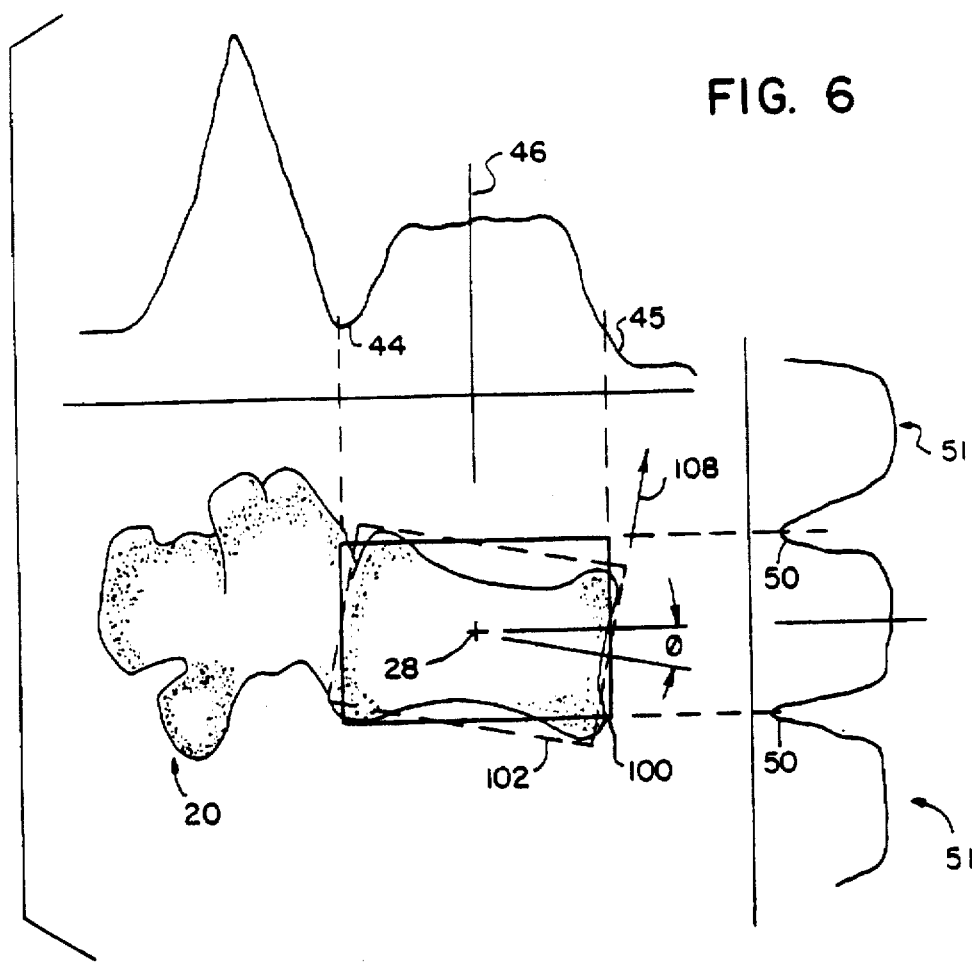
FIG. 6 is an illustration of a vertebra and its vertical and horizontal histograms similar to FIGS. 2, 3 and 4 showing a first method of determining an analysis axis.

Referring now to FIG. 3, a horizontal histogram is constructed along each anterior-posterior line of the scan pattern for vertebrae L2-L4. The horizontal histogram of FIG. 3, like the vertical histogram of FIG. 4, has as its vertical axis bone mineral density. The horizontal axis of the histogram of FIG. 3 is the number of an anterior-posterior scan line. Also like the vertical histogram of FIG. 4, the horizontal histogram has local minima 44. The local minimum 44 represents the approximate posterior border 32 of the vertebra 21 located between the maxima created by the posterior elements 38 and the maxima created by the major portion (i.e. the body) of the vertebra 21 itself. Minimum 45 indicates the approximate anterior border of the vertebra 21. Thus the center 28 of each vertebrae 20 may be approximated as illustrated in FIG. 6 as the intersection of the scan line in the anterior-posterior direction which is halfway between points 44 and 45 and the superior-inferior center 53 of the vertebra 21 which is halfway between the local minimum 50 of the vertical histogram.

Referring now to FIG. 5, once the center 28 of each vertebrae L2-L4 has been detected as indicated by process block 64, a coordinate system is established aligned to each vertebrae 20. Referring now to FIG. 6, a rectangular area 100 may be established about the center 28 of each vertebrae 20 having an anterior-posterior width equal to the distance between minima 44 and 45 and having a superior-inferior height equal to the distance between minima 50. As defined, the rectangular area 100 will be aligned with its sides parallel or perpendicular with the scans of raster scan 17 or the scan direction 19.

The PBM data elements within the rectangular area 100, are then summed to produce an alignment value. This alignment value indicates roughly the total bone mass of the vertebral body 21 within rectangle 100 and is thus a general measure of the "fit" of the rectangle 100 to the vertebral body 21.

A new rectangle 102 is then created also centered about point 28 but perturbed by angle f and a new alignment value is calculated. If the perturbed rectangle 102 produces a lower alignment value, a new perturbed rectangle 102 is generated with a rotation in the opposite direction. If, however, a higher alignment value is obtained with perturbed rectangle 102, a further rectangle 102 is generated with additional angle f and a new alignment value calculated. This process is repeated until there is detected a decrease (after an increase) in alignment value within the perturbed rectangle 102.

Thus, rectangle 102 is gradually rotated in one way or the other until the alignment value is maximized. It is found that the orientation of rectangle 102 which gives the highest alignment value is also the orientation which maximizes the amount of vertebral body 21 contained within borders of rectangle 102. Thus, upon completion of the rotation process, the rectangle 102 is a best fit of a rectangle 102 to the vertebral body 21 and establishes a coordinate system for analyzing the vertebral body 21 morphology. Specifically, all measurements of the vertebral body 21 are taken along parallels to the vertical or horizontal edges of the rectangle 102. A column axis 108 parallel to the vertical edge of rectangle 102 is identified to indicate this axis of measurement as distinguished from the scan direction 19.

Figure 7:
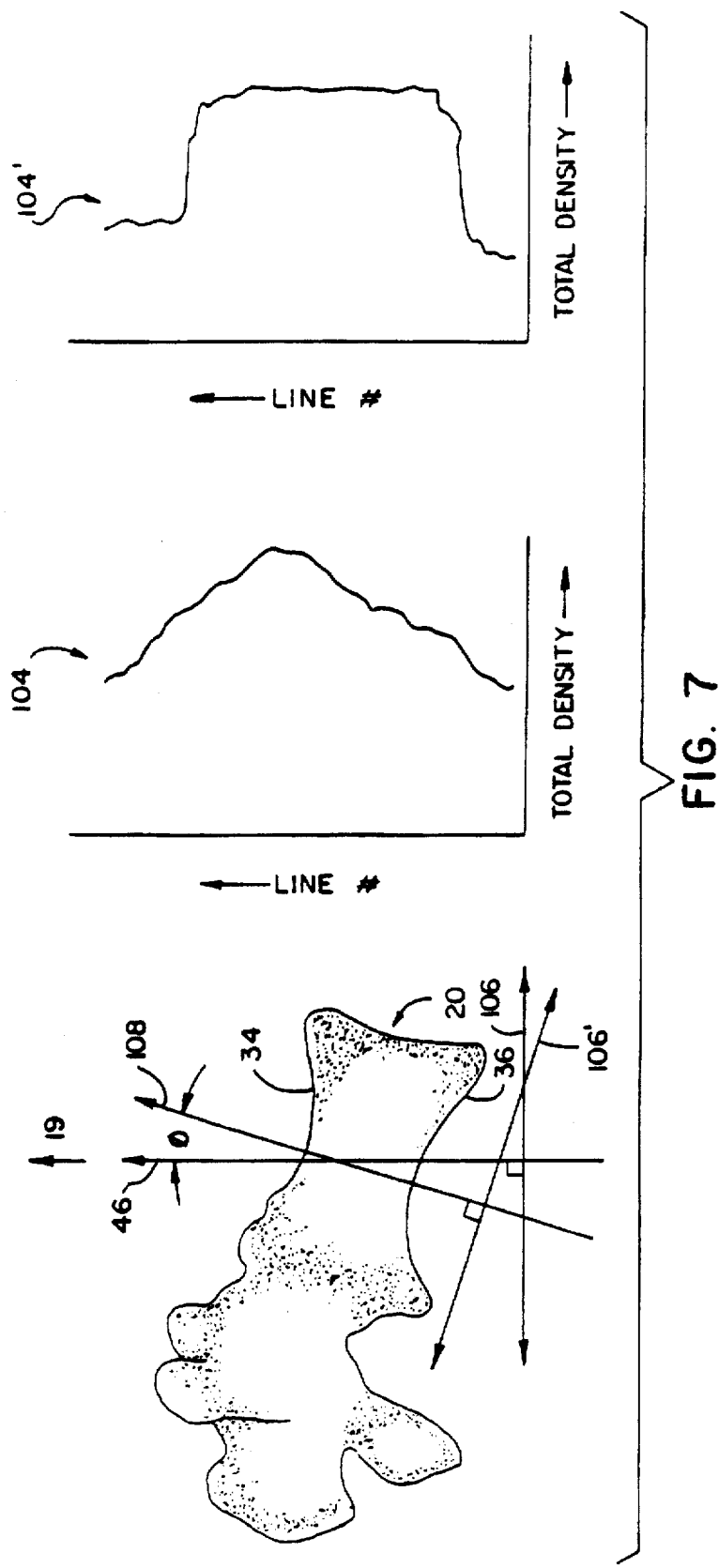
FIG. 7 is an illustration of a vertebra showing corresponding histograms taken along two different axes showing a second method of determining an analysis axis.

Alternatively, and in a second embodiment shown in FIG. 7, the coordinate system for the measurement of vertebral morphology may be established by creating a column averaged histogram 104 taken along line 46 in the scan direction 19. The vertical axis of the column averaged histogram is a line number of a row of data elements, and the horizontal axis of the column averaged histogram is the total density of the data elements of that row, that is, the sum of the data element in that row. For a vertebra 20 tipped with respect to the scan direction 19, the column averaged histogram 104 will exhibit a relatively low rate of change as a result of the obliquely advancing rows of data elements extending along arrow 106 which cross the inferior border 36 and superior border 34 at an angle. In a manner similar to that described with respect to FIG. 6, a new column axis 108 is iteratively generated and canted with respect to the scan direction 19 by an angle f. A new column averaged histogram 104' is generated with respect to this column axis 108. If the row orientation 106' of the new column axis 108 better aligns with the inferior border 36 and the superior border 34 of the vertebral body 21, the column averaged histogram 104' will exhibit a more rapid rate of change in total row bone density with respect to row number. The derivative of the column averaged histogram 104' may be taken and the peak value of the derivative compared between column averaged histograms 104 with other column axes 108 (at different angles f) to select a column axis 108 that produces the greatest such derivative value within a limited angular range. This column axis 108 is selected as the reference axis for future morphological measurements.

Thus, although the scan direction 19 may not be aligned with the vertebral body 21, so that the anterior and posterior borders 30 and 32 are substantially parallel to the scan direction 19 and the superior border 34 and inferior border 36 substantially perpendicular to the scan direction 19, a new column direction 108 may be determined and measurements of the vertebrae morphology taken with respect to that column direction 108 to provide improved accuracy and repeatability in the measurement of the vertebrae morphology. This alignment of a coordinate represented by column axis 108 to each vertebra is indicated at process block 68 of FIG. 5.

Figure 8:
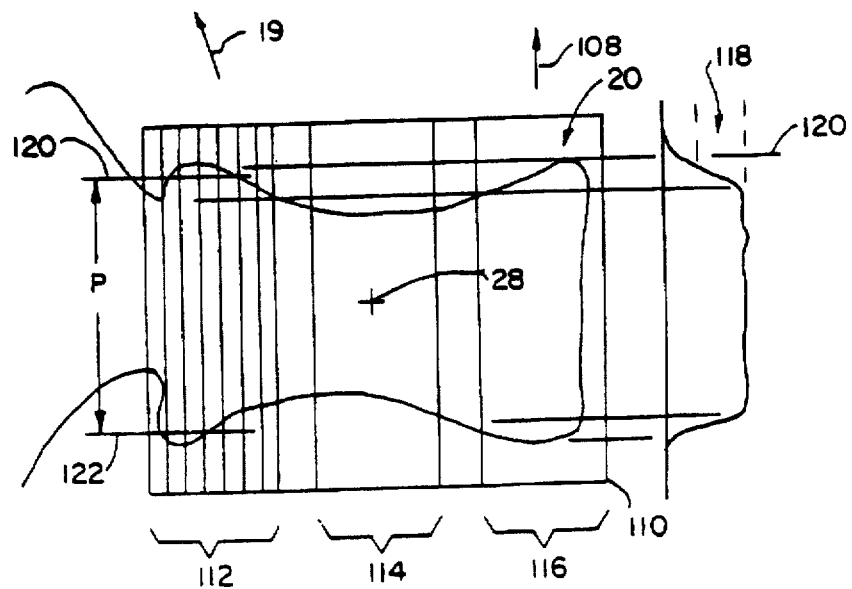
FIG. 8 is a lateral view of a vertebra aligned with the analysis axis showing the generation of measurement zones over which vertebral height is averaged in preparation to analyzing the morphometry of the vertebra.

Referring now to FIG. 8, in general, the column direction 108 will differ from the scan direction 19. Once the column direction 108 has been determined for a given vertebral body 21, the data elements are effectively "rebinned" to comport with that new coordinate system. The rebinning may be accomplished by generating a new series of locations within the vertebral body 21 corresponding to evenly spaced lines and columns aligned with the new column axis 108. Interpolated data elements lying on these locations at the new columns and rows are obtained by a bilinear interpolation of the nearest neighbor actual data elements weighted according to the actual locations of those data elements. New vertical and horizontal histograms are then constructed from these interpolated data elements much in the manner as described with respect to FIG. 6 with the horizontal histogram displaying average density for a vertical column of interpolated data elements and the vertical histogram displaying the average density for a row of the interpolated data elements.

Referring to FIG. 8, the minima of the horizontal and vertical histograms are used to derive an analysis rectangle 110 in the same manner as that described with respect to the rectangle 100 of FIG. 6, the analysis rectangle 110 being aligned with the column axis 108 and encompassing principally the vertebral body 21 and not the posterior elements 38. This analysis rectangle 110 is then divided by the computer into zones as indicated by process block 68 of FIG. 5. In the preferred embodiment, three zones are selected, a posterior zone 112, a medial zone 114 and an anterior zone 116. In the preferred embodiment, the zones are rectangular having an anterior to posterior width of ¼ that of the analysis rectangle 110 and extending the full height of the analysis rectangle 110 in the superior to inferior direction and evenly spaced therein. The relative width and number of zones is arbitrary and can be varied according to values entered by the user and the dimensions of the analysis rectangle 110.

In the example of FIG. 8, the posterior, medial and anterior zones define a set of data elements that will be employed to produce fiducial measurements with respect to the morphology of the vertebral body 21. The first set of such measurements is to determine the average height of that portion of the vertebral body in the superior to inferior direction of each of the three zones of the analysis rectangle 110.

In one embodiment, this is done by starting with the posterior zone 112; the data elements within the zone are automatically summed across rows by the computer to produce a zone histogram 118. The vertical axis of the zone histogram 118 is a row number of data elements corresponding to an anterior-posterior row and the horizontal axis is the total bone mass of the data elements of that row and within the posterior zone 112. This zone histogram 118 differs from the other histograms described thus far in that it is effectively focused on the posterior zone 112 and thus sensitive to the morphology of that region alone.

A first row 120 is automatically identified by the computer on that histogram, and thus with respect to the vertebral body 21, at the rising edge of the histogram 118 associated with the superior border 34 in the posterior zone 112. A number of criteria may be employed in selecting this first row 120, such as, the first row having a bone mass value to exceed a fixed predetermined threshold. In the preferred embodiment, the row is selected as that which has a PBM value first exceeding 30% of the peak histogram value of the zone histogram 118. Ideally, the computer selects as a first row 120 the row which best approximates the position of the superior border 34 if the position of its contour in the posterior zone (as weighted by PBM value) were averaged out. In actual practice a deviation of the selected first row 120 from the true average of the superior border 34 is not significant as long as the same criteria is used each time in selecting the first row 120 and hence constancy of measurement is obtained.

Likewise, a second row 122 is selected from the histogram 118 in its inferior border 36 in the posterior zone 112. Here the falling edge of the histogram 118 is examined and the second row 122 selected as that row which first fails below 30% of the maximum PBM value for the histogram 118. The distance between these rows 120 and 122 is automatically determined and termed the posterior height and represented by P and is assumed to be the average height of the vertebral body in the region of the posterior zone.

Each of the other zones, the medial zone 114 and the anterior zone 116 are likewise analyzed by generating a zone histogram 118 and identifying two rows, one at the superior border 34 and one at the inferior border 36. The distance between columns for the medial zone becomes the medial height M and for the anterior zone becomes the anterior height A. The extractions of these morphological height values is indicated in FIG. 5 as process block 70.

In the preferred embodiment, the height values A, M, and P are calculated by multiplying the number of rows of data elements between the first row 120 and the second row 122 for each zone by the distance between each row of data elements in the analysis rectangle 110. That distance between rows of data points is a characteristic of the digital imaging technique used, and will be known. The computer will automatically perform the above described analysis on each zone of the analysis rectangle.

In an alternative embodiment, the average height of each zone is determined by the computer by automatically identifying in each zone, data pairs; one data element of each pair corresponding to a location on the superior border and the other data element corresponding to a location on the opposite, inferior border. The two data elements of each pair have a relationship to one another such that an imaginary line transecting each data element of a data pair would be reasonably parallel to the column axis 108. Each data element of a data pair is selected by the computer by performing a local comparison of the PBM values of data elements. For example in selecting data elements lying on the superior border, the computer would examine the PBM values of adjacent elements. As illustrated in FIG. 9 a data element 111 having neighboring data elements of similar value in the anterior, posterior and inferior orientations but of markedly lesser value in the superior orientation would be assumed to lie at or near the superior border. In like manner the computer will automatically examine all the data elements in the top ⅓ position of zone 112 to determine those data elements lying on the superior border. Once data elements on the superior border had been selected, a similar analysis would be conducted on the data elements in the lower ⅓ portion of zone 112 to select data elements lying on or near the inferior border portion of zone 112. With data elements selected on each border the computer would then pair data elements on the superior border with data elements on the inferior border by assigning the data elements to columns reasonably parallel to column axis 108. Having organized the data elements into pairs and assigned the pairs to columns the computer employs an algorithm to automatically determine the distance between each element in a pair by multiplying the number of data elements found between each element of a data pair by the distance between each data element. As stated above the distance between data elements is a characteristic of the digital imaging technique used. The distance between data elements of a pair is taken as the inferior to superior height of the vertebral body 21 at the particular location of the column associated with that pair.

Having determined the height of all the columns in zone 112, the heights are summed and an average height is obtained for zone 112. In similar fashion average heights are obtained for the medial zone 114 and the anterior zone 116.

By a similar process, the analyses rectangle 110 may be divided into several (preferably three equal) horizontally extending fiducial zones (not shown) and columns identified at the anterior and posterior borders 30 and 32 of the vertebral body 21 to determine the average widths of such horizontally extending fiducial zones. In the preferred embodiment, three zones, a superior zone S, central zone C and inferior zone I are selected and automatically measured.

In each zone S, C and I, an anterior column and a posterior column is identified in a process analogous to that described above with respect to the selection of the first and second rows 120 and 122 of a posterior zone 112, a medial zone 114 and an anterior zone 116. A center column is also determined for the zones S, C and I being exactly half way between the anterior and posterior identified columns. The intersection of the identified columns of the zones S and I and the rows posterior zone 112, a medial zone 114 and an anterior zone 116 define a set of fiducial points. For example, the intersection of the first row 120 for the posterior zone 112 and the first column for zone C defines one such fiducial point.

The identified columns of the zones S, C and I also serve to create measures S, C, and I corresponding to measures A, M, and P, as described above, but extending in an anterior-posterior direction.

Thus it will be understood that fiducial points at the "corners" and center superior and inferior borders 34 and 36 of the vertebral body 21 may be established and that the separation of these fiducial points with respect to one another measured automatically. Although each of these fiducial points has a specific location, they represent an average of the BMD values of the surrounding data points and hence are robust against small errors in the BMD measurements at any given data point.

Once the computer has identified these fiducial points, the computer automatically uses this data to accurately define the shape and size of the vertebra being studied which, at the option of the operator can be displayed visually such as on a CRT device or a printing device. More importantly, however, the computer is programmed to use the data regarding shape and size to formulate indicia of vertebral condition having clinical or diagnostic value and then to visually display the indicia for use by the operator either in diagnosing a clinical condition or increasing the accuracy of bone density measurements if such measurements are being made.

Determining the Measured Index

Measures A, M, and P of vertebra L2–L4 are then used to prepare a measured index for subsequent analysis of the vertebral column. The values of A, M and P for each of vertebra L2 through L4 are averaged together for each vertebrae L2–L4 to produce a vertebral height for each vertebrae. Alternatively, the average values of A, M and P can be used separately to scale the corresponding measures of the set of standard values and each of the measured values of A, M and P can be compared to the values of A, M and P of the scaled set of reference values. Each of these vertebral heights for L2–L4 are then compared to an average of all vertebral heights for L2–L4 and if the individual heights deviate below the average height by more than a predetermined amount, the deviant vertebra is excluded from the calculation of the measured index, as will now be described, under the assumption that such deviation indicates the particular vertebra was fractured.

This average of the vertebral heights is then recomputed disregarding any fractured vertebrae to produce the measured index for that individual.

The Set of Reference Values

A vertebral morphometric data is collected from healthy individuals of the same sex and having similar height and weight, and this data for corresponding vertebra in each individual is averaged together to produce standard A, M and P values for each vertebra of a set of reference values. The measures of this set of reference values are stored within the computer 18. The value of A, M and P for this set of reference values and for vertebra L2–L4 is then averaged to produce a standard index for the set of reference values.

At the conclusion of the vertebral measurement of the spine of an individual, the corresponding measures for vertebra of the set of reference values will be displayed for reference. Prior to display, however, the set of reference values are multiplied by the ratio of the measured index to the standard index so as to scale the measurements of the set of reference values to be comparable to the particular individual whose spine is being analyzed. This scaling relies on the recognition varying though spines of individuals have varying vertebral heights, the relationship of vertebral heights within a given individual tend to be consistent ratios.

The resulting normalized set of reference values displayed in conjunction with the measured vertebral heights of the patient provide a convenient reference for a physician. Thus, for example, if a given vertebra of L2 of the set of reference values is 25 mm and its standard index is 23 mm but the measured index of the individual being analyzed is 22 mm (indicating that the vertebrae of the individual are generally smaller than those of the set of reference values) the value of L2 of the set of reference values is normalized by the fraction $22/23$ prior to display.

Ideally, no additional information such as weight, height, ethnicity or sex need be provided for the measured individual thus reducing the possibility of error in the entry of this data and reducing or eliminating the need for multiple standards.

Alternatively, of course, the same effect may be produced by normalizing the measured values of vertebral heights for the individual, in this case by the ratio of the standard index to the measured index, to provide effective vertebral heights for the individual that may be compared directly to the unmodified set of reference values. If desired, the difference between the measured vertebral morphometric measurement and the corresponding value for the set of reference values, or similar indication of deviation may be calculated and presented to the user.

Other Vertebrae

The vertebral heights of the remaining vertebrae beyond L2 through L4 may be obtained by a similar process as described above. Alternatively this process may be modified to improve the robustness of the automatic vertebral height determination—particularly for vertebrae partially obscured by ribs in the upper thoracic region. In this alternative embodiment, the measured index is applied to the set of reference values which is then mapped on the actual data acquired for the individual being measured. This mapping may be displayed to the user by the superposition of intervertebral lines 302 over the image of the measured spine based on the standard of the previous identification of the centers of the vertebrae. Because this set of reference values has been scaled by the measured index developed from vertebra L2 through L4, the intervertebral lines 302 will be expected to closely match the intervertebral space of the measured individual.

Referring again to FIG. 4, the vertical histogram for the vertebra superior to L2 through L4 may now be windowed by analyses zones 302 based on lines 304 bisecting the vertebral spaces of the set of reference values. The analyses zones are simply a predetermined amount above and below the lines 304.

The process then proceeds as has been described with respect to process blocks 64–70 of FIG. 5 with the computer constrained to find vertebral centers outside of the zones 302 but to detect the vertebral endplates for the determination of measures A, M and P within the zones 302. More specifically, superior fiducial points must be within a zone 302 and below line 304 whereas inferior fiducial points must be within a zone 302 and above line 304. The automated process is thus guided away from potentially misleading edges outside of the vertebral endplates such as may be caused by ribs or the like.

The height of the analyses zones 302 is selected so that deviations between the set of reference values and that of the actual individual will still cause the superior and inferior endplates to fall within the defined regions.

Semi-Automatic Constraints

It will be recognized that this approach of constraining the automatic fiducial point identification process may also be employed by placing the constraints manually rather than through the use of the normalized set of reference values as has been described. With such a manual procedure, the user would identify lines 302 with the cursor control device for example by drawing lines 302 separating the vertebra running substantially through the intervertebral space. Alternatively, this line could be drawn along the inferior or superior endplate of a vertebra or vertebrae. A curved line could also be drawn. Alternatively, two or more points could be placed on the image to identify a line or curve for the same purpose. The user input is limited to at most several dozen lines or a few dozen points. A combination system, employing lines drawn with reference to the set of reference values that may then be moved or modified by the user, strikes a compromise between these two approaches. In all cases computer analysis is used to determine which pairs of points are subject to study as morphometric lengths and distances between the fiducial points subject to review by the user.

Evaluation of Vertebral Morphometric Data

Using the invention described herein, measurements can be automatically obtained for a single vertebra, or can be obtained for several vertebrae. It is possible to use the analysis performed by the algorithm for several purposes. This analysis is most effectively directed to the vertebral body, that is the portion of the vertebra excluding the posterior element. Various measurements of a vertebral body which are obtained by the invention herein described can be used to provide indicia of disease or deformity as described below. Additionally, the measurements obtained of a single vertebral body can be compared to those of adjacent vertebral bodies, as determined from a single scan, to determine if one or more vertebrae has been subjected to a trauma or other incident which produces an abnormality in that vertebra. Of course as described above, the indicia of a vertebral body can be compared to the normalized set of reference values. Another alternative is that the indicia for the vertebral bodies can be compared from time to time in the same individual, to show changing vertebral morphology over time, which can be indicative of the progress of clinically significant conditions.

EXAMPLE 1

Anterior Height

A particular indicia of interest for vertebral morphology is anterior height of the vertebra. It has already been described above, in connection with the description of the fiducial points, how the algorithm automatically calculates the distance from inferior border to superior border for each fiducial zone. The anterior height of the vertebral body is the distance between the two end plates, or the distance between the superior border and the inferior border at or adjacent to the anterior border. In the prior art, the point at which the anterior height of the vertebra was preferably measured was within the first 5 to 10 mm from the extreme anterior border of the vertebral body. In the preferred embodiment of the present invention a fiducial zone 116 is selected which occupies the anterior ¼ portion of the analysis rectangle 110 and within this zone the computer determines an average height of the anterior portion of the vertebral body 21. If compared with the prior art technique of selecting a particular point for measurement of anterior height, the technique of the present invention which automatically determines an average height within a preselected fiducial zone is found to be superior in terms of reproducibility. This anterior height A, as determined by the present invention, may be displayed to an operator in absolute units of measurement, such as millimeters, or the computer can provide height relative to the average height of the other vertebrae of that patient or the corresponding vertebra in the set of reference values.

EXAMPLE 2

Posterior Height

Another indicia of interest is the measurement of posterior height P of the vertebra. Like anterior height, posterior height measurements made in the prior art are taken at a single location within 5 to 10 mm of the posterior border of the vertebra. The present invention provides an automatic measurement of the average height of the posterior region of the vertebral body 21 lying within the posterior fiducial zone 112 which occupies the posterior ¼ of the analysis rectangle 110. Like anterior height, posterior height may be displayed to an operator in absolute units of measurement, such as millimeters, or the computer can provide height relative to the average height either of the other vertebrae oft hat patient or the corresponding value of the set of reference values.

EXAMPLE 3

Anterior/Posterior Height Comparison

An important indicia which the computer can be programmed to automatically obtain is a comparison of anterior height A to posterior height P. Typically a 15% decrease in anterior vertebral height, either relative to a norm, relative to the same individual in previous measurements, or relative to the posterior height of the same vertebra, is taken as an index of anterior vertebral fracture, a clinically significant indication.

EXAMPLE 4

Wedge Angle

Another indicia of vertebral morphology which can be automatically obtained with the present invention is the wedge angle. The wedge angle of the vertebra is defined as the degree of departure from a parallel relationship that linear extensions of the planes of averages of the inferior and superior borders would create. In the prior art, this is calculated based on the overall anterior and posterior height of the vertebra. From these values of anterior and posterior height and from the distance between the locations at which the measurements were taken, it becomes possible to calculate the angle between hypothetical straight lines extending through the superior and inferior borders of the vertebra. In the present invention, the distance between A and P for purposes of plotting the wedge angle is C. Since A, P and C are average values, variability in the wedge angle due to variation in the selection of the location for height and width measurement is avoided. Typically a 15° wedge angle of a vertebra is taken to indicate that wedge fracture has occurred in the vertebra. A wedge fracture is a recurrent clinical condition, observed as a modality of vertebral fracture recognized in clinical literature.

EXAMPLE 5

Biconcavity Index

Another indicia of vertebral morphology which the computer of the present invention can be programmed to automatically measure is referred to as the biconcavity index. The index of biconcavity of the vertebral body is calculated by comparing the degree to which the height of the central portion of the vertebral body deviates from the average height of the posterior and anterior borders of the body. In other words, this is measuring the deformation of the vertebral body as it tends to become a concave object. This biconcavity indicates a degree of deformation of the vertical body associated with relatively poor vertebral condition. This quantity can be calculated automatically by the computer which uses an algorithm to compare M to the average of A and P. M can also be compared to adjacent vertebrae, or to average values from a normal reference population previously obtained. A 15% preferential decrease in central height of the vertebral body as compared to the anterior and posterior borders is often taken to represent a central fracture or a condition of biconcavity.

EXAMPLE 6

Hypertrophy

Another indicia of vertebral morphology which the computer of the present invention can be programmed to measure is hypertrophy of the end plates oft he vertebrae or hypertrophy of nodes located within the vertebra. Hypertrophy refers to a condition where portions of the vertebral body have a relative density which is abnormally greater than that typically seen with other vertebrae. In conventional densitometry, localized areas of high or low density are ignored and only larger area averages are obtained. This can lead to misleading interpretations of bone mineral levels when discontinuities are present as caused by hypertrophy. The ability of the present invention to define and reproducibly locate a variety of zones: the posterior zone 112, the medial zone 114, the anterior zone 116 and zones S, C, and I, allow bone density to be evaluated separately at a variety of places within the vertebra. By comparing the bone density in S or I zones to the C zone, for example, end plate hypertrophy may be detected. Alternatively, a hypertrophied node, may be detected by evaluating the bone density over the entire region within the fiducial points at the "corners" of the vertebra to identify any data points, or a small set of data points, within that defined area that have values which differ by more than a predefined amount from the statistical norm of all the values within that area.

While this indicia is not generated specifically for clinical value, in and of itself, it is useful insofar as it represents information about a region of vertebrae having unique characteristics which must be excluded from otherwise valid measurements of bone density or mineral content. For this reason, it may be used to provide a warning to the operator indicating that the bone mineral data for a particular vertebra may need close review.

EXAMPLE 7

Intervertebral Spacing

Intervertebral spacing may be readily determined from the evaluation of the fiducial points at the superior border of one vertebra and the inferior border of the next superior vertebra. Essentially, the intervertebral spacing is the distance between the corresponding fiducial points for these two vertebrae.

As a result of the possible difference in column axes 108 for the two vertebrae, the intervertebral distance may preferably be evaluated by considering the average distance between two edges, one defined by line segments joining the fiducial points at the superior border of the inferior vertebra, and the other defined by line segments joining the fiducial points at the inferior border of the superior vertebrae.

EXAMPLE 8

Warning of Defective Verterbra

It is specifically intended that the indicia of morphological character of the vertebral body, whether height, compression, wedge, or biconcavity, are utilized by the instrument for two discreet purposes. One purpose is to create a warning to the operator that the bone mineral density data for a particular vertebra should not be utilized since it may be inappropriate. It can readily be understood that a porous bone if crushed will have a higher measured density than a porous bone which has not been subject to crushing. In that instance, the higher density of the crushed bone is not an indication of the health of that bone, quite to the contrary. Accordingly, it is appropriate for the instrument of the present invention to create an indicational warning to the operator as indicated by process block 76 in FIG. 5 in when one or more of the indicia of significant vertebral body fracture have been detected. In any event, the result is that a heightened accuracy of bone mineral density calculation is obtained by the bone densitometer, as well as providing the benefit of potential diagnosis of clinically significant conditions of vertebral deterioration.

The calculation of these various indicia from the measurements of A, M, and P, and S, I and C and their separation is indicated in process block 72 of FIG. 5. At subsequent process block 76 an indication may be presented to the operator of abnormal indications which have been detected by the method, if any. The abnormal conditions can be indicia described above which are outside the normal values to be expected for patients of the category of the patient who has been scanned. If such an indication has occurred, the operator will then know that the average value for bone density for the particular vertebrae having the discontinuity should not be utilized for clinical purposes.

EXAMPLE 9

Predicting Vertebral Fracture

A decrease in bone mass, or the presence of one or more vertebral fractures, is associated with an increase in the likelihood of future vertebra fractures. A decrease in bone mass of two standard deviations is associated with an increase of four to six times in the likelihood of future vertebral fractures whereas the existence of two fractures, as determined by a morphologic measurement of anterior height or A is associated with an increase of twelve times in the likelihood of future vertebral fractures. See, Ross, et al., "Pre-Existing Fractures and Bone Mass Predict Vertebral Fracture Incidence in Women", *Annals of Internal Medicine*, v. 114–11:919 (1991).

A combination of bone mass measurement and morphometric evaluation of fracture is associated with an increase of seventy-five times in the likelihood of future vertebral fractures and provides correspondingly improved predictive power. The present invention, which allows a densitometer to be used in making morphometric measurements, should prove valuable in conveniently providing both bone mass and fracture data for such combined measurements.

EXAMPLE 10

Dual Angle Morphology and BMD Measurement

Referring to FIG. 10, prior to the lateral scan of the patient 16, an anterior posterior dual energy scan may be performed with the x-ray source 12 in position 100 as rotated about the patient 16 on C-arm 14. As is understood in the art, dual energy scanning provides an improved ability to distinguish between x-ray attenuation caused by tissue as opposed to bone allowing more accurate BMD determinations, but also provides less accuracy for morphology measurements. The anterior-posterior positioning of the C-arm 14 also improves the bone density measurement to the extent that the amount of intervening tissue is reduced at that angle.

Referring also to FIG. 5 the BMD values obtained from the anterior to posterior scan may be employed to calculate BMD as indicated by process block 78 and to calculate bone area as indicated by process block 80 according to techniques well known in the art. Rather than directly displaying the BMD values however, a lateral scan is then performed with the x-ray source 12 at position 100 so that the axis of radiation 24 is horizontal. The calculated values of BMD for various points in the anterior-posterior scan of the patient may be matched approximately to those corresponding points in the lateral scan and the indicia of the morphometric measurements of a given vertebra 20 may be matched to the calculated BMD values of process block 80 and bone area values of process block 82. If the indicia for a given vertebra are abnormal, then at process block 84, where BMD and area calculations may be displayed, a suitable warning may be given to the operator that the BMD values and area values are suspect as indicated by process block 76.

The correlation of anterior to posterior scanned points to lateral scanned points simply matches the longitudinal coordinates of each such point and makes the assumption that the patient has not shifted on the table appreciably between scans. Alternatively, the intervertebral zones 40 may be derived for each of the anterior posterior and lateral scans and the data from each scan shifted to correlate the histograms of each scan so that the intervertebral zones 40 match.

The ability to use a densitometer to make morphologic measurements is critical to this augmentation of BMD and bone area calculations by morphometric indicia as it allows both measurements to be made without shifting the patient.

The indicia calculated at any one time for a patient may be compared to subsequent or previous determinations on the same patient. By such comparison, changes in vertebral morphology over time can be tracked. In addition, the digital image obtained at subsequent determinations following an initial determination may be subtracted from the stored initial image to produce a differential image. The boundary conditions used for determining morphological indicia may be used to precisely overlap such sequential images.

Alternatively, the indicia calculated for a patient may be compared to values contained in a data base of reference values categorized by sex, age or other criteria.

The following embodiments illustrate the use of the invention to make morphological measurements of the femur, hip joint, and metacarpal bones of the hand. It is to be understood that these examples are illustrative only and do not limit the invention in any way. In particular, it should be appreciated that the measurements described for the femur and metacarpal may be applied to other bones and joint spaces, such as the shoulder, for example, in a human being or an animal body.

Femoral Studies

Figure 12:
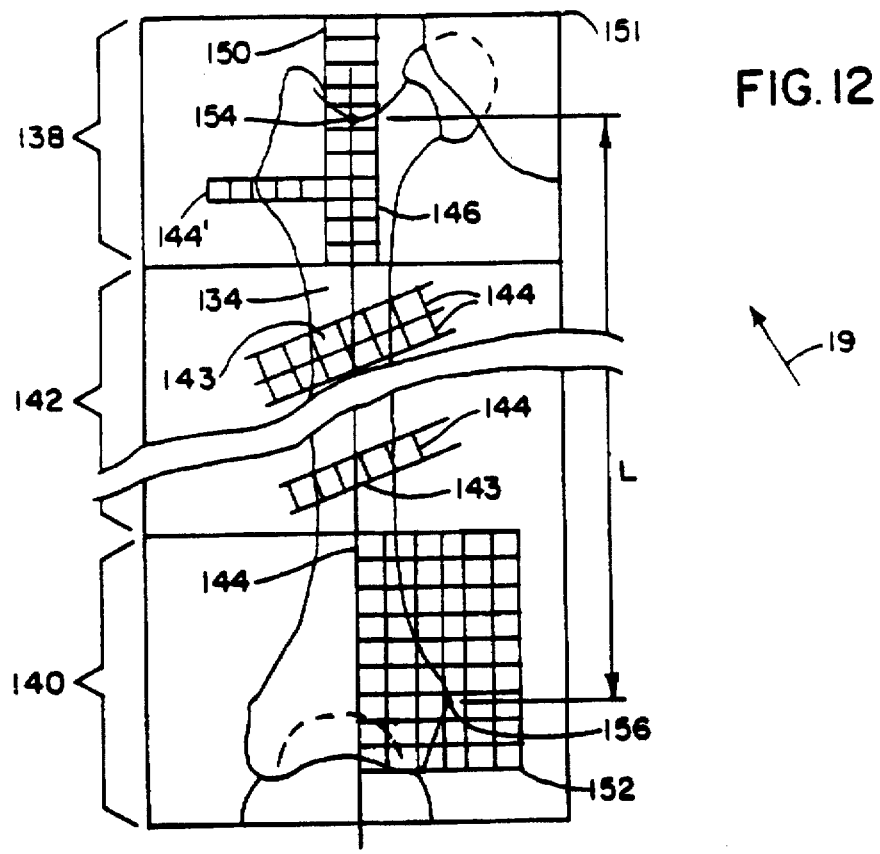
FIG. 12 is an illustration of an anterior-posterior view of a femur showing the determination of the femur's axis and the identification of fiducial points at the proximal and distal ends.
Figure 14:
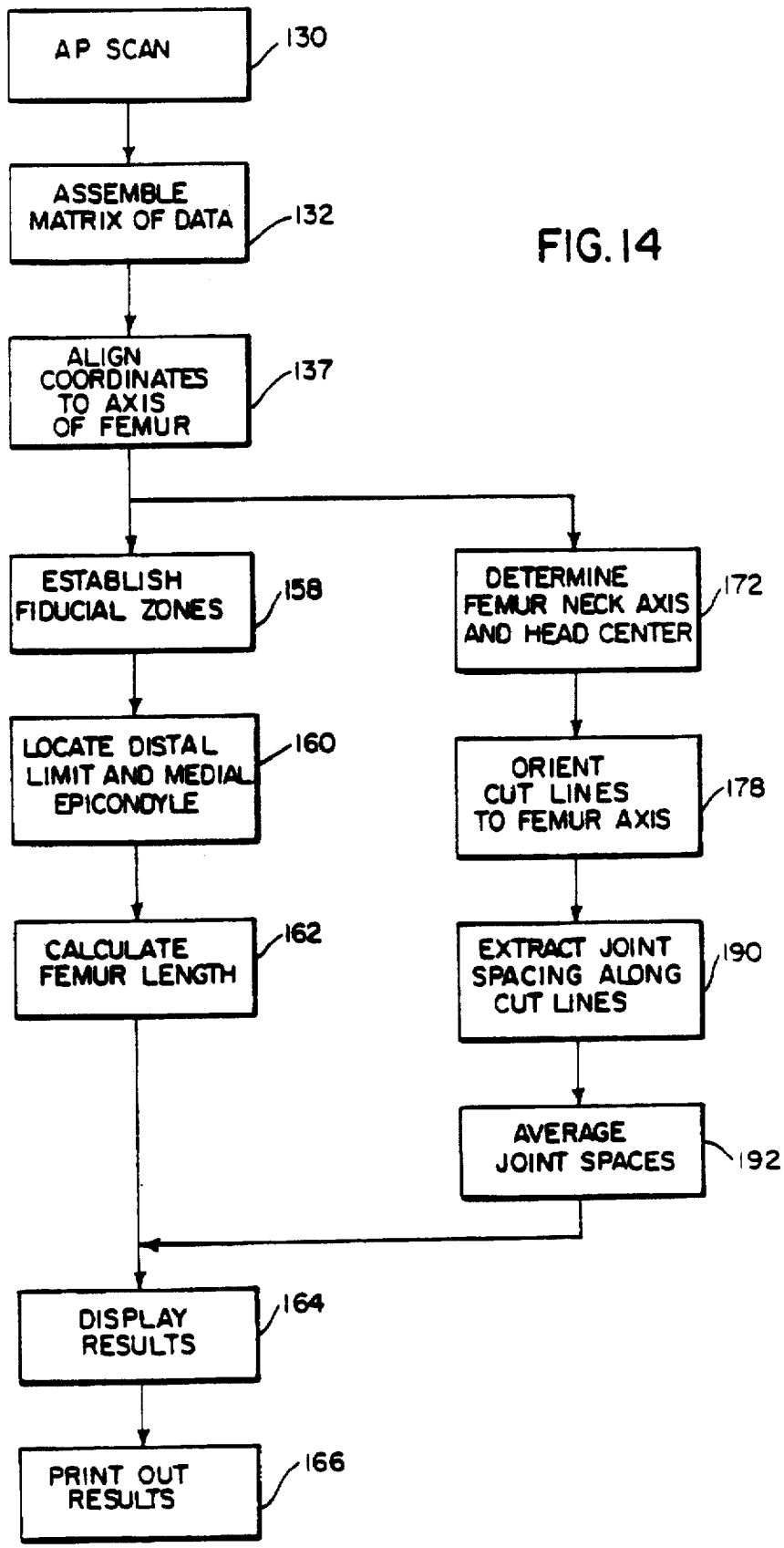
FIG. 14 is a flow chart similar to that of FIG. 5 showing the method of the present invention in measuring limb length and joint spacing.

Referring to FIGS. 12 and 14, in studying the human femur 134 it is preferred that the scan be taken from an anterior-posterior (AP) direction through the femur 134. The AP scan is indicated by process block 130. Once the scan has been completed, the data acquired in the scan is again assembled into a matrix of data values within the computer 18 as generally indicated by process block 132. Each data value within the matrix indicate the relative absorption of x-rays at each point of the scan. Thus the matrix provides both absorption data and location data.

As described above with respect to FIG. 3, after completion of the scan, the computer 18 automatically conducts a local comparison of data elements to determine the juncture of the data elements attributable to bone and data elements attributable to soft tissue. The threshold for the distinction between bone and soft tissue is determined by means of a histogram as has been described.

Generally, the scan direction 19 will not be perfectly aligned with the orientation of the femur 134. Instead, the angle between the long axis of the femur 134 and the scan direction 19 will vary among patients 16 and even among different studies of the same patient 16.

Although this variation may be compensated for by a physician observing radiographs of the femur 134, differences between the orientation of the femur 134 and the scan direction 19 can cause unacceptable variation in automated measurement of morphometric values.

Accordingly, the first step in the morphometric analysis of the femur 134 is a determination of the axis 146 of the femur as indicated generally by process block 137. The axis 146 substantially bisects the shaft of the femur 134 along its long axis and may serve as a reference for subsequent measurements. As will be understood, because the determination of the position of the axis 146 is determined by a large number of data values, the location of the axis 146 should be reproducible even in studies separated by considerable periods of time.

Determining the location of the axis 146 of the femur 134 requires that the matrix of data acquired be truncated by the operator, or according to automatic methods, to that data 151 contained within a rectangle roughly circumscribing the entire femur with a limited inclusion of other adjacent bones. Further, the femur axis 146 must be approximately oriented along the scan direction 19. This selection and orientation is typically accomplished setting the limits and orientation of the AP scan per process block 130.

Once the relevant data is selected, a top portion 138 is identified including the superior one-sixth of the selected data 151 as measured along the scan direction. Similarly, a bottom portion 140 including an inferior one-sixth of the selected data 151 is identified. The remaining central portion 142, including approximately two-thirds of selected data 151 generally excludes the ends (epiphyses) of the femur and include only the shaft (diaphysis).

In the central portion 142, each row 144 of data is analyzed and the center data value 143 of the bone values for that row 144 determined. The orientation of each row 144 (exaggerated in FIG. 12 for clarity) is perpendicular to the scan direction 19 but generally not perpendicular to the long axis of the femur 134.

The process of identifying the centermost bone value for each data element in the rows 144 is repeated until a set of centers 143 are 134. A line fit to shaft of the femur 134. A line fit to these centers 143 establishes the femur axis 146. As noted above, the femur axis 146 provides a more reproducible reference for subsequent measurements than the scan axis 19.

Once the femur axis 146 has been established, the data values of the matrix are rebinned, as has been previously described, so that the data values follow rows 144' and columns perpendicular and parallel to the femur axis 134.

Referring still to FIGS. 12 and 14 once the femur axis 146 has been located, two measurement zones 150 and 152 are established, per process block 158, in order to identify fiducial points of the proximal limit 154 and the medial epicondyle 156. The former measurement zone 150 extends in a superior direction approximately from the beginning of the superior portion 138 (as determined from the rebinned data values) along the femur axis 146.

Within this measurement zone, per process block 160, each rebinned row 144' is examined to find the superior most row 144' still having bone values and aligned with the femur axis 146. This row is considered to be the height of the femur 134 and contains the proximal limit 154 and forms one endpoint for the measurement of the length of the femur 134.

The second measurement zone 152 extends in an inferior direction from the beginning of the inferior portion 140 and proximally from the femur axis 146. The position of the medial epicondyle 156 is considered to be the break in the smooth curve of the femur surface joining the diaphysis to the epiphysis. This break point may be determined by considering the first derivative of row value of the medial-most data element in each row 144 of the measurement region 152 identified to bone, as one progresses in an inferior direction. The first row 144' where the derivative goes to zero is considered the location of the medial epicondyle 156. This row 144' is taken as the second endpoint in the determination of the length of the femur 134.

Per process block 162, the femur length L may be calculated by subtracting the row coordinates for the two rows endpoints embracing the proximal limit 154 and the medial epicondyle 156.

Once the femur length L has been calculated, the results may be displayed per process block 164 or printed out per process block 166 via the computer 18 and display 22. The length L may be displayed as a function of time, through the compilation of a number measurements over a period of time or may be compared to a database of "normals" as previously described with respect to the vertebral measurements.

The length of the femur may be used to provide an indication of bone growth. Thus, it is of primary importance that measurements of femur length taken years apart may be accurately compared. The use of the fiducial points centered around the medial epicondyle and the proximal limit 154 is intended to provide such reproducibility. The referencing of the measurements to the femur axis 146 which is located by the mathematical combination of a large mount of data within region 142 helps ensure this reproducibility.

Figure 13:
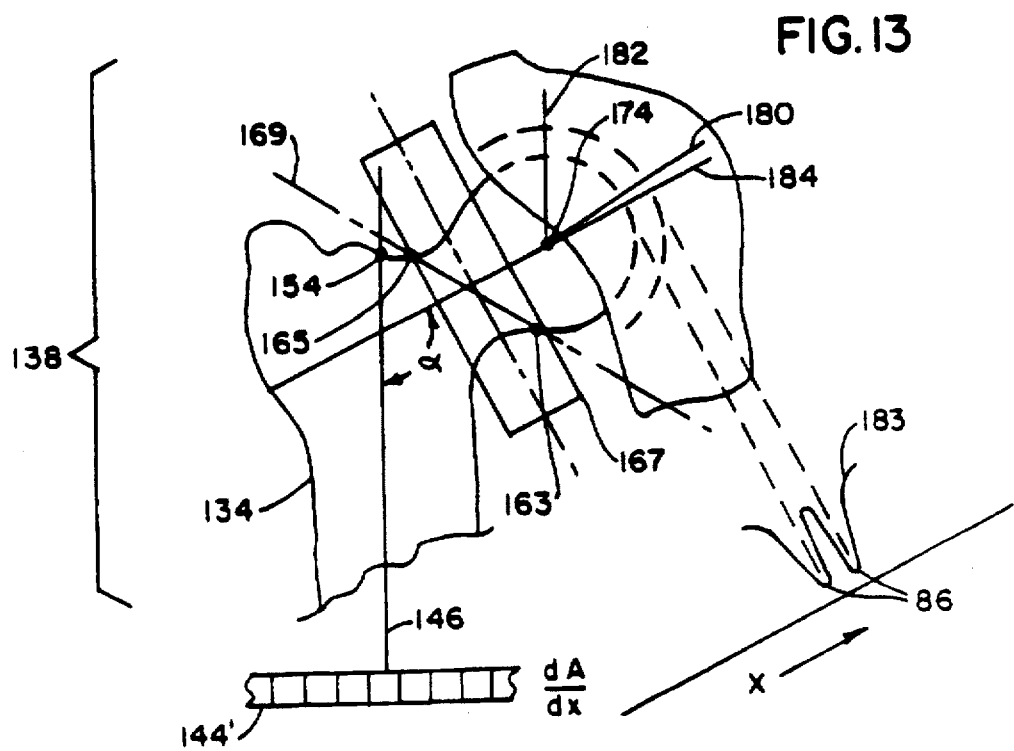
FIG. 13 is an anterior-posterior view of the interface between the femur head and the acetabulum showing the placement of cut lines to determine joint spacing positioned relative to a graph showing rate of change in x-ray attenuation along one cut line used for the calculation of joint spacing.

Referring to FIGS. 13 and 14, a second measurement, of the joint spacing between the femur head 170 and the acetabulum 168, may be performed on the femur 134. The measurement of joint spacing may permit the evaluation of joint function and the tracking of degenerative joint disease such as arthritis. Again, when measurements must be made over a period of time it is imperative that variability caused by changes in the measurement technique, rather than the joint spacing, be reduced to a minimum.

The joint spacing begins again with the determination of the femur axis 146, as has been previously described with respect to process blocks 130, 132, and 137, to provide a reproducible reference. Once the femur axis 146 has been identified, the data in the superior zone 138 and the medial side of the femur axis 146 is analyzed on a row by row basis, starting at the inferior edge of the superior zone 138 to identify an inferior and superior inflection point 163 and 165 respectively. The inferior inflection point 163 is the center of the last isolated tissue data elements in a row 144' having bone values flanking them. Thus, inferior inflection point 163 is the highest point of the downward concavity of the femur neck. If two such points occur, in a given row, the point closest to the femur axis 146 is selected.

The superior point of inflection 165 is the center of the first detected isolated tissue elements having bone values flanking them after the inferior inflection point 163 as progressively superior rows of data 144' are examined. The superior point of inflection 165, then, is the lower most point of the upward concavity of the femur neck.

These points are determined at process block 172 in preparation for determining a femur neck axis 184 of the femur neck and a center 174 of the femur head.

Once points 163 and 165 are determined, a measurement rectangle 167 having a width of one centimeter and a length of four centimeters is aligned with an inflection axis 169 passing through the points 165 and 163 such that the inflection axis 169 is coincident with the long axis of the measurement rectangle 167 and so that points 165 and 163 are equidistant from the center of the measurement rectangle 167.

Data elements within the measurement rectangle 167 are organized into rectangle rows along the rectangle's width and rectangle columns along the rectangle's length in a manner analogous to the rebinning described with respect to process block 137 and rows 144. The data elements of the measurement rectangle 167 are then analyzed to determined a centerline (not shown) across the width of the measurement rectangle 167 and symmetrically bi-secting the bone elements contained within the measurement rectangle 167. Specifically, each column of data in the measurement rectangle 167 is analyzed to find the centermost element within that column and a line is fit to those center points. This centerline approximates the femur neck axis 184, that is, the line of symmetry of the extension of the femur's neck.

Once this centerline is determined, the measurement rectangle 167 is rotated so that its axis of symmetry along its width is aligned with this centerline. This realignment typically involves a translation and rotation of the measurement rectangle 167.

As rotated, the new data within the measurement rectangle 167 is arranged in rows and columns with respect to the measurement rectangle and that data is analyzed to determine the column having the minimum length of contiguous bone elements among all columns within the measurement rectangle 167. This column corresponds roughly to the narrowest portion of the femur neck within the measurement rectangle 167. The measurement rectangle 167 is then moved along its short axis, and thus generally along the axis 184 of the femur neck, so as to position this determined minimum width of the neck approximately at the center column of the measurement rectangle 167.

The determination of the centerline of the bone data within the columns of data of the measurement rectangle is then repeated and the measurement rectangle shifted again to align its short axis with this centerline and the measurement rectangle is again moved to position the shortest column of bone data at its centermost column in an iterative fashion. These two steps of repositioning the measurement rectangle 167 are repeated until the incremental adjustments drop below a predetermined amount or until predetermined number of times so that the measurement rectangle's short axis is coincident with the axis 184 of the femur neck and the measurement rectangle is positioned straddling the narrowest portion of the neck.

The position of the femur neck axis 184 is set equal to the short axis of the measurement rectangle 167, thus positioned.

For the purpose of measuring joint spacing and certain other dimensions, an average width of the femur neck is determined from the length of the bone elements in the centermost column of data of the measurement rectangle 167. Next, a centerpoint 174 corresponding approximately to the center of the femur head is identified along the femur neck axis 184 displaced from the center of the measurement rectangle 167 by the measured neck width. This calculation reflects an approximation that the radius of the femur head is equal to the average width of the femur neck.

Minor variations in this location of the center point 174 may be tolerated because of the primary reliance on the location of the femoral axis 146.

At process block 178 cut lines 180 and 182 radiating from the center 174 are established based on a neck axis 184 and femur axis proceeding from the center 174. Cut line 182 is parallel to femur axis 146 and cut line 180 is spaced from cut line 182 by 60 degrees in a clockwise direction.

Between cut lines 180 and 182 five more cut lines are defined (not shown) proceeding from center point 174 and spaced at every 10 degrees about that center point 174.

The values of the attenuation "A" of x-rays indicated by the data values of the matrix may be determined along each cut line by bilateral interpolation as is well understood in the art. The derivative 183 of these attenuation values (dA/dx) as a function of a distance x along the individual cut lines is then determined starting at the center point 174 and proceeding outward from the head 170 of the femur, at process block 190.

The distance between the first two minima 186 of the derivative 183 along each cut line is taken as the joint spacing for that cut line and the joint spacings for all cut lines are averaged, at process block 192, to produce an average joint spacing. The joint spacing may be displayed and printed out per process blocks 164 and 166 or may be compared to normals contained in a data base of such values.

The ability to fix this measurement of joint spacing with respect to a robust reference of the femur axis 146 and to average a number of values of joint spacing improves the reproducibility of this measure.

Certain of the measurements obtained by these studies may be used for the purposes of evaluating the strength of the hip joint. For example, the angle between the femur axis 146 and the femur neck axis 184, together with the distance between the intersection of these two axes and the center 174 of the femur head, and the width of the femur neck provide a measure of the mechanical strength of the neck under the weight of the patient 16.

These measurements may also be performed on a patient 16 having an artificial hip joint so as to provide an indication of any possible shifting of the prosthetic joint with respect to the femur 136. This shifting may be characterized by the distances between the center 174 and the intersection of the femur axis 146 and the femur neck axis 184, or the distance between this latter point and the intersection of the femur neck axis 184 with the lateral most portion of the femur 134.

Metacarpal Studies

Figure 15:
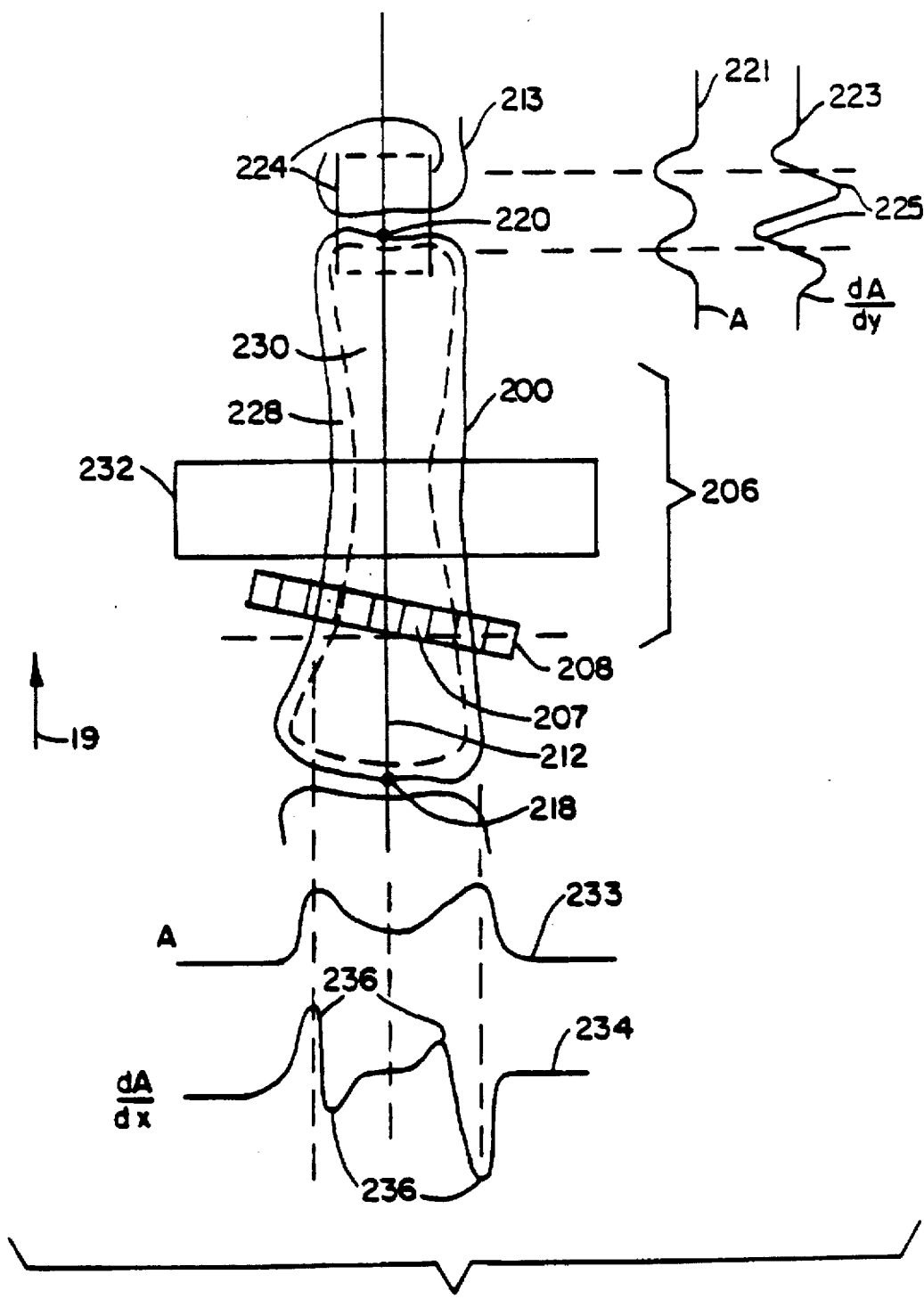
FIG. 15 is a planar view of a metacarpal bone of a human hand showing the determination of a reference axis with respect to measurements of cortical to trabecular bone and joint spacing within the hand.
Figure 16:
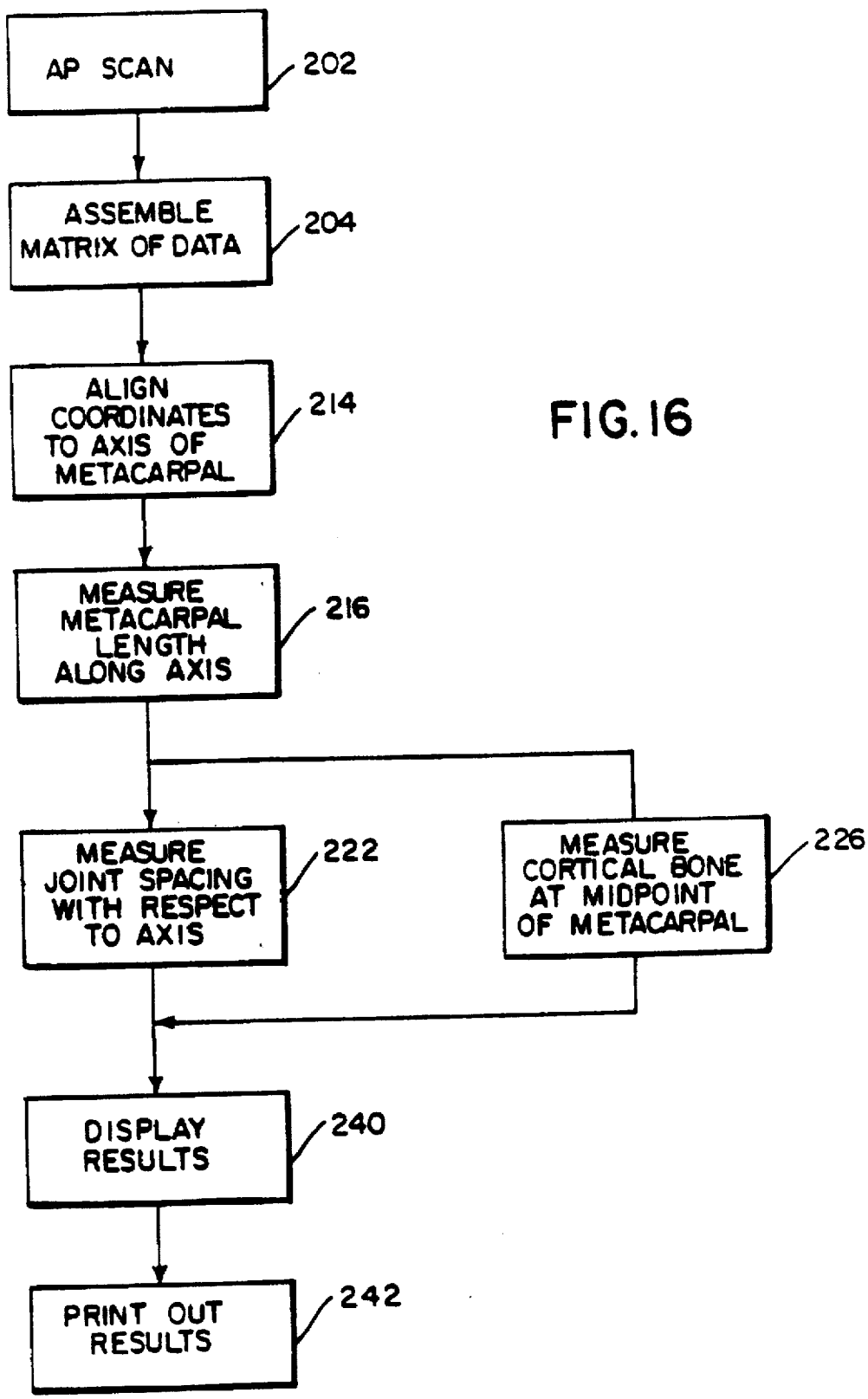
FIG. 16 is a flow chart similar to that of FIG. 14 showing the steps of obtaining the measurements shown in FIG. 15.

Referring now to FIGS. 15 and 16, similar studies to those described with respect to the femur 136 may be advantageously made of the human hand and in particular of the third metacarpal bone 200 (center finger) of the human hand.

Like the femur, it is preferred that the scan of the hand be taken in anterior/posterior direction with the hand in the anatomic position, that is, from the back of the hand through the palm of the hand, per process block 202. Again, the scan data is assembled into a matrix of data values within computer 18 as generally indicated by process block 204.

The third metacarpal bone 200 to be measured is generally identified by the operator by selecting a point on the metacarpal bone 200 and selecting that data related to the third metacarpal by connectivity algorithms known in the art. Alternatively, this selection process may be performed automatically.

Generally, the hand of the patient 16 is oriented so that the metacarpal bone 200 extends along the columns of scan data indicated by arrow 19. However, it will be understood, as described above, that the columns of scan data will not necessarily align with the axis of the metacarpal bone 200. For this reason, in a manner analogous to those described above, coordinates are first established with respect to the metacarpal bone 200.

In particular, once the data elements have been isolated into bone or soft tissue and according to those associated with the metacarpal 200, a center portion 206 of the data of the metacarpal 200 is selected and the centermost bone value 207 of each row 208 within this center portion 206 is identified and aligned fit to those centers 207 indicating the metacarpal axis 212. As with the femur, the center portion of the data used for the determination of the metacarpal axis 212 may be the center two thirds of the rows of the scan matrix.

Once this metacarpal axis 212 is determined, the data values are rebinned, as has been described, so that subsequent measurements may be made with respect to this axis 212. This rebinning is indicated at process block 214.

The metacarpal length is readily determined, per process block 216 by reviewing the rebinned data along the column aligned with metacarpal axis 212. A distal point 220 is determined by moving distally from the center region of the metacarpal 200 along the metacarpal axis 212 until the first non-bone value is detected, that non-bone value corresponding to cartilage between the metacarpal and the proximal phalanx 213. Likewise, a proximal point 218 is determined by moving proximally from the center region of the metacarpal 200 along the metacarpal axis 212 until the first non-bone value is detected.

Joint spacing between the distal epiphysis of the metacarpal 200 and the opposing face of the proximal phalanx 213 may next be determined, as indicated by process block 222 by evaluating the rebinned data symmetrically located on either side of the metacarpal axis 212 by a predetermined range indicated by lines 224 and proceeding distally until the first bone values are detected in each column of rebinned data after the end of bone values of the metacarpal 200. The total non-bone data contained between the bones of the metacarpal 200 and the proximal phalanx 213 is then divided by the number of columns within the range of lines 224 to provide a joint spacing having the robustness of a statistical average.

Yet another measurement that may be advantageously made once the data has been rebinned is that of conical thickness as indicated by process block 226. Within the data of the metacarpal 200 as isolated from soft tissue by the histogram process previously described is a denser conical layer 228 and a less dense trabecular center 230. The relative proportions of these two portions 228 and 230 may provide a more sensitive measure of the change in bone structure than for example the thickness of the metacarpal 200. This measurement involves differentiating between these two different bone types within the data acquired.

The first step in such measurements is to position the measurement rectangle 232 at the center of the metacarpal 200. The measurement rectangle 232 has a width, oriented along the axis of the metacarpal 200, of 0.5 cm and a length of 2.0 cm. Each column of data values 233 within the measurement rectangle 232, aligned across the metacarpal axis, is differentiated to produce a derivative graph 234. The positive and negative peaks 236 of this graph 234 are taken as the locations of the interfaces between soft tissue and cortical bone and between conical bone and trabecular bone. These locations are averaged for each column of the data of the measurement rectangle 232 to provide average measurements of conical and trabecular thickness.

The results of process blocks 216, 222, and 226 may be displayed and printed out for review per process blocks 240 and 242. The values may be reviewed directly or compared to statistical norms contained within a data base of standard value.

It is thus envisioned that the present invention is subject to many modifications which will become apparent to those of ordinary skill in the art. For example, all automated processes anticipate certain degrees of user interaction and verification and although the preferred embodiment contemplates an automatic system, claims should not be construed to exclude the ability of the user to review and override automatically identified points.

Accordingly, it is intended that the present invention not be limited to the particular embodiment illustrated herein, but embraces all such modified forms thereof as come within the scope of the following claims.

I claim:

1. A method of evaluating the integrity against fracture of a vertebra in an animal or human, the vertebra having a superior and inferior margin and anterior and posterior margin, comprising the steps of:

(a) scanning the vertebra with a beam of radiation to acquire a matrix of discrete data elements each having a value wherein each said data element corresponds to a defined location in the area of said vertebra, and wherein the value of each data element is related to a physical property of the material of the vertebra or its surrounding tissue;

(b) reviewing the values of the data elements and their defined locations to identify at the edge of the vertebra one or more pairs of fiduciary points and measuring the distance between the points to produce a morphometric measure;

(c) measuring the absorption of the beam of radiation through the vertebra to produce a value related to the bone mass of the vertebra; and (d) displaying the morphometric measure and the value related to the bone mass of the vertebra so as to indicate the likelihood of future vertebral fractures in the vertebra.

2. The method of claim 1 wherein the step of reviewing of the values of the data elements takes the average of plurality of data elements weighted by their position to determine each fiduciary point.

3. The method of claim 1 where the morphological measure is selected of the group consisting of:

anterior height (A), medial height (M), posterior height (P), superior width (S), center width (C), inferior width (I).

4. A method of evaluating the osteoporosis in a vertebra in an animal or human, the vertebra having a superior and inferior margin and anterior and posterior margin, comprising the steps of:

(a) scanning the vertebra with a beam of radiation to acquire a matrix of discrete data elements each having a value wherein each said data element corresponds to a defined location in the area of said vertebra, and wherein the value of each data element is related to a physical property of the material of the vertebra or its surrounding tissue;

(b) reviewing the values of the data elements and their defined locations to identify at the edge of the vertebra one or more pairs of fiduciary points and measuring the distance between the points to produce a mophometric measure;

(c) measuring the absorption of the beam of radiation through the vertebra to produce a value related to the bone mass of the vertebra; and (d) displaying the morphometric measure of the value related to the bone mass and the vertebra so as to indicate an osteoporotic condition of the vertebra.

5. The method of claim 4 wherein the step of reviewing of the values of the data elements takes the average of plurality of data elements weighted by their position to determine each fiduciary point.

6. The method of claim 4 where the morphological measure is selected of the group consisting of:

anterior height (A), medical height (M), posterior height (P), superior width (S), center width (S), inferior width (I).

* * * * *

UNITED STATES PATENT AND TRADEMARK OFFICE
CERTIFICATE OF CORRECTION

PATENT NO. : 5,673,298
DATED : September 30, 1997
INVENTOR(S) : Richard B. Mazess It is certified that error appears in the above-identified patent and that said Letters Patent is hereby corrected as shown below:

Col. 11, line 58, "fails"        Should be --falls--

Col. 14, line 1, "vertebra"      Should be --vertebrae--

Col. 17, line 42, "oft he"       Should be --of the"

Col. 21, line 15, "are 134."     Should be --are established along the long shaft of the femur 134--.

Col. 24, line 52, "matfix."      Should be --matrix.--

Col. 25, line 43, "value."       Should be --values.--

Signed and Sealed this

Seventh Day of April, 1998

Attest:

Attesting Officer

BRUCE LEHMAN

Commissioner of Patents and Trademarks